US006924295B2

(12) United States Patent
Tajima et al.

(10) Patent No.: US 6,924,295 B2
(45) Date of Patent: Aug. 2, 2005

(54) TETRAHYDROQUINOLINE DERIVATIVE COMPOUND AND DRUG CONTAINING THE COMPOUND AS ACTIVE INGREDIENT

(75) Inventors: Hisao Tajima, Mishima-gun (JP); Yoshisuke Nakayama, Mishima-gun (JP); Tadashi Tatsumi, Mishima-gun (JP); Daikichi Fukushima, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 11 days.

(21) Appl. No.: 10/481,103

(22) PCT Filed: Jun. 17, 2002

(86) PCT No.: PCT/JP02/06005

§ 371 (c)(1), (2), (4) Date: Dec. 18, 2003

(87) PCT Pub. No.: WO02/102780

PCT Pub. Date: Dec. 27, 2002

(65) Prior Publication Data

US 2004/0171835 A1 Sep. 2, 2004

(30) Foreign Application Priority Data

Jun. 18, 2001 (JP) ....................................... 2001-184068

(51) Int. Cl.[7] .................... C07D 215/02; C07D 401/02; A61K 31/47

(52) U.S. Cl. ........................ 514/311; 514/314; 546/183

(58) Field of Search ................................. 514/311, 314; 546/183

(56) References Cited

U.S. PATENT DOCUMENTS 5,780,480 A 7/1998 Wai et al.
6,121,282 A 9/2000 Dominianni et al.

FOREIGN PATENT DOCUMENTS

EP 1 108 713 A1 6/2001
WO WO 99/15520 A1 4/1999

*Primary Examiner*—Zinna Northington Davis
(74) *Attorney, Agent, or Firm*—Sughrue Mion, PLLC

(57) ABSTRACT

A compound of formula (I)

(I)

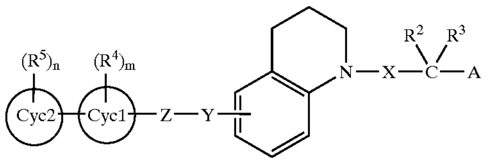

(wherein all symbols are as defined in the specification) and salt thereof, and peroxisome proliferator activated receptor regulator comprising thereof as active ingredient. Because a compound of formula (I) have an activity of regulating peroxisome proliferator activated receptor regulator, the compound of formula (I) is useful as a hypoglycemic agent, a hypolipidemic agent, a preventive and/or treatment agent for diseases associating metabolic disorders (diabetes, obesity, syndrome X, hypercholesterolemia, hyperlipoproteinemia, etc.), hyperlipemia, atherosclerosis, hypertension, circulatory diseases, overeating, coronary heart diseases, etc., an HDL cholesterol-elevating agent, an LDL cholesterol and/or VLDL cholesterol-lowering agent and a drug for relief from risk factors of diabetes or syndrome X.

11 Claims, No Drawings

SEQUENCE LISTING

```
<160> NUMBER OF SEQ ID NOS: 3

<210> SEQ ID NO 1
<211> LENGTH: 85
<212> TYPE: DNA
<213> ORGANISM: Artificial Sequence
<220> FEATURE:
<223> OTHER INFORMATION: Enhancer sequence including four times
      repeated Gal4 protein
      response sequences

<400> SEQUENCE: 1

tcgacggagt actgtcctcc gcgacggagt actgtcctcc gcgacggagt actgtcctcc     60

gcgacggagt actgtcctcc gagct                                           85


<210> SEQ ID NO 2
<211> LENGTH: 9
<212> TYPE: PRT
<213> ORGANISM: Simian virus 40

<400> SEQUENCE: 2

Ala Pro Lys Lys Lys Arg Lys Val Gly
1               5


<210> SEQ ID NO 3
<211> LENGTH: 9
<212> TYPE: PRT
<213> ORGANISM: Influenza virus

<400> SEQUENCE: 3

Tyr Pro Tyr Asp Val Pro Asp Tyr Ala
1               5
```

TETRAHYDROQUINOLINE DERIVATIVE COMPOUND AND DRUG CONTAINING THE COMPOUND AS ACTIVE INGREDIENT

TECHNICAL FIELD

The present invention relates to tertrahydronaphthalene derivative compounds.

More specifically, the present invention relates to (1) tetrahydroquinoline derivative compounds represented by formula (I)

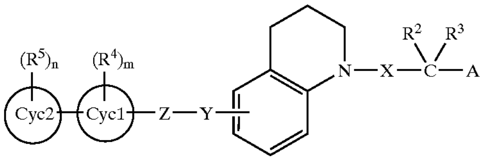

(wherein all symbols have the same meanings as described below), or nontoxic salts thereof, (2) a process for preparing thereof, and (3) an agent comprising thereof as an active ingredient.

BACKGROUND ART

Recently in the study of transcription factors concerned with marker genes expression in adipocytes differentiation, peroxisome proliferator activated receptor (abbreviated as PPAR hereinafter), which is one of intranuclear receptors, has been focused. cDNAs of PPAR were cloned from various kinds of animals, and plural isoform genes were found, particularly in mammals three types of isoforms (α, δ, γ) are known (see J. Steroid Biochem. Molec. Biol., 51, 157 (1994); Gene Expression., 4, 281 (1995); Biochem Biophys. Res. Commun., 224, 431 (1996); Mol. Endocrinology., 6, 1634 (1992)). PPAR γ isoform is predominantly expressed in adipose tissues, immune cells, adrenal gland, spleen, small intestine. PPAR α isoform is mainly expressed in adipose tissue, liver, retina, and PPAR δ isoform is widely expressed without specificity for tissue (see Endocrinology., 137, 354 (1996)).

On the other hand, the following thiazolidine derivatives are known as agents for the treatment of non-insulin dependent diabetes mellitus (NIDDM) and are hypoglycemic agents which are used for the improvement of hyperglycemia in the patients suffering from diabetes. They are also effective for the improvement of hyperinsulinemia, glucose tolerance and decrease of serum lipid and therefore they are thought to be considerably hopeful as agents for the treatment of insulin resistance.

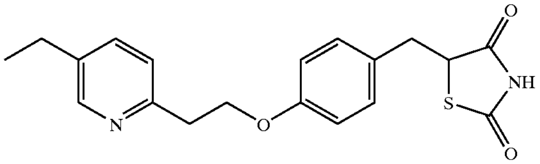

pioglitazone

-continued

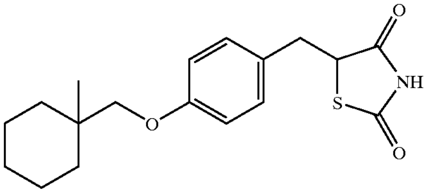

ciglitazone

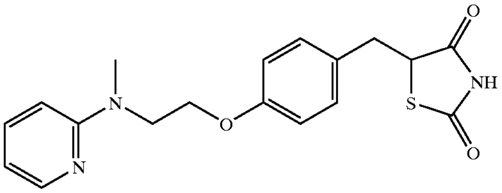

BRL49653

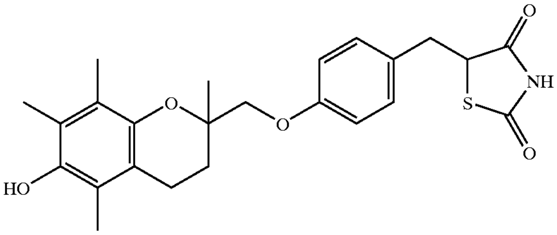

troglitazone

One of the target proteins in the cells of these thiazolidine derivatives is exactly PPAR γ and it is resolved that they enhance the transcription activity of PPAR γ (see Endocrinology., 137, 4189 (1996); Cell., 83, 803 (1995); Cell., 8, 813 (1995); J. Biol. Chem., 270, 12953 (1995)). Therefore, a PPAR γ activator (agonist) which enhances its transcription activity is thought to be hopeful as a hypoglycemic agent and/or a hypolipidemic agent. Furthermore, since a PPAR γ agonist is known to promote the expression of PPAR γ protein itself (Genes & Development., 10, 974 (1996)), an agent which increases the expression of PPAR γ protein itself as well as PPAR γ activating agent is also thought to be clinically useful.

PPAR γ is related to adipocytes differentiation (see J. Biol. Chem., 272, 5637 (1997) and Cell., 83, 803 (1995)). It is known that thiazolidine derivatives which activate this receptor promote adipocytes differentiation. Recently it was reported that thiazolidine derivatives increase fat mass and cause man to gain weight and to become obese (see Lancet., 349, 952 (1997)). Therefore, it is also thought that antagonists which inhibit PPAR γ activity and agents that decrease the expression of PPAR γ protein itself are also clinically applicable. On the other hand, a compound that phosphorylates PPAR γ protein and decreases its activity is reported (Science., 274, 2100 (1996)). This implies that an agent which does not bind on PPAR γ protein as a ligand, but inhibits its activity is also clinically applicable.

From these, PPAR γ activators (agonists) and PPAR γ regulators for its expression that can increase the expression of the protein itself are expected to be useful as hypoglycemic agents, hypolipidemic agents, and agents for prevention and/or treatment of diseases associated with metabolic disorders such as diabetes, obesity, syndrome X, hypercholesterolemia and hyperlipoproteinemia etc., hyperlipidemia, atherosclerosis, hypertension, circulatory diseases and overeating etc.

On the other hand, antagonists that inhibit the transcription activity of PPAR γ or PPAR γ regulators that inhibit the expression of the protein itself are expected to be useful as hypoglycemic agents and agents for prevention and/or treatment of diseases associated with metabolic disorders such as diabetes, obesity and syndrome X etc., hyperlipidemia, atherosclerosis, hypertension and overeating etc.

The following fibrate compound (e.g. chlofibrate) is known as a hypolipidemic agent.

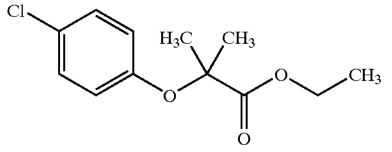

chlofibtate

And, it is also resolved that one of the target proteins in the cells of fibrate compounds is PPAR α (see Nature., 347, 645 (1990); J. Steroid Biochem. Molec. Biol., 51, 157 (1994); Biochemistry., 32, 5598 (1993)). From these facts, PPAR α regulators which can be activated by fibrate compounds are thought to have a hypolipidemic effect, and so they are expected to be useful as agents for prevention and/or treatment of hyperlipidemia etc.

Besides, it has been recently reported that PPAR α possesses anti-obese activity in the specification of WO 9736579. In addition, it was reported that the elevation of high density lipoprotein (HDL) cholesterol level and the reduction of low density lipoprotein (LDL) cholesterol, very low density lipoprotein (VLDL) cholesterol and triglyceride levels were induced by activation of PPAR α (J. Lipid Res., 39, 17 (1998)). It was also reported that composition of fatty acids in blood, hypertension and insulin resistance were improved by administration of bezafibrate which is one of fibrate compounds (Diabetes., 46, 348 (1997)).

Therefore, agonists that activate PPAR α and PPAR α regulators that promote expression of PPAR α protein itself are useful as hypolipidemic agents and agents for treatment of hyperlipidemia, and are expected to have HDL cholesterol level-elevating effect, LDL cholesterol and/or VLDL cholesterol levels-lowering effect, inhibition on the progress of atherosclerosis and anti-obese effect. Therefore, they are thought to be hopeful agents for the treatment and/or prevention of diabetes as hypoglycemic agents, for the improvement of hypertension, for the relief from risk factor of syndrome X and for the prevention of occurrence of ischemic coronary diseases.

On the other hand, few reports are found on ligands that activate PPAR δ significantly or on biological activities associated with PPAR δ. PPAR δ is sometimes called PPAR β, or it is also called NUC1 in humans. Until now, as for activity of PPAR δ, it is disclosed in the specification of WO 9601430 that hNUC1B (PPAR subtype whose structure is different from that of human NUC1 in one amino acid) inhibited the transcription activities of human PPAR α and thyroid hormone receptor. Recently in the specification of WO 9728149, it was reported that the compounds, which possessed high affinity to PPAR δ protein and which could activate PPAR δ significantly (i.e. agonists) were found out and that they had HDL (high density lipoprotein) cholesterol level-elevating activity. Therefore, agonists that can activate-PPAR δ are expected to have HDL cholesterol level-elevating effect, and so they are expected to be useful for the inhibition on the progress of atherosclerosis and treatment thereof, as hypolipidemic agents and hypoglycemic agents, for the treatment of hyperlipidemia, as hypoglycemic agents, for the treatment of diabetes, for the relief from risk factor of syndrome X, and for the prevention of occurrence of ischemic heart diseases.

For example, the specification of WO98/00403 discloses that an isoquinoline derivative represented by formula (A)

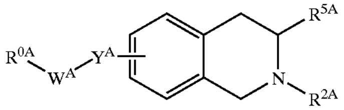

(A)

(wherein, $A^{0A}$ is

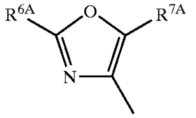

(i)

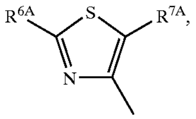

(ii)

etc., $R^2$A is hydrogen atom, C1–4 acyl, etc., $R^5$A is COOH, etc., $R^6$A is hydrogen atom, C1–4 alkyl, aryl, etc., $R^{7A}$ is hydrogen atom, C1–4 alkyl, etc, $W^A$ is $(CH_2)_{nA}$, $Y^A$ is O, S, etc., nA is integer of 1–4) or a salt thereof are useful for the treatment of hyperglycemia and hyperlipidemia (necessary parts were extracted from the description of groups).

DISCLOSURE OF THE INVENTION

In order to find a compound having a PPAR modulating activity, the present inventors have conducted intensive studies and found, as a result, that the objects can be accomplished by the compound represented by formula (I), and thus the present invention has been accomplished.

The present invention relates to (1) A tetrahydroquinoline derivative compound represented by formula (I)

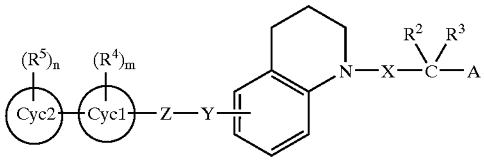

wherein

A represents (1) —COOR$^1$, or 1H-tetrazol-5-yl, $R^1$ represents (1) hydrogen atom, or (2) C1–10 alkyl, $R^2$ and $R^3$ each independently represent (1) hydrogen atom, or (2) C1–10 alkyl, or taken together with the carbon atom to which they are attached, represents C3–7 cycloalkylene, X represents (1) bond, or (2) C1–3 alkylene, Y represents (1) —O—, or (2) —S—, Z represents C1–4 alkylene, Cyc1 and Cyc2 each independently represents (1) partially or fully optionally saturated C3–15 mono-, bi-, or tri-carbocyclic aryl, or (2) partially or fully optionally saturated 3–15 membered mono-, bi- or tri-heterocyclic aryl containing 1–4 hetero atom(s) selected from oxygen, nitrogen or sulfur atom, $R^4$ and $R^5$ each independently represents (1) C1–10 alkyl, (2) C2–10 alkenyl, (3) C2–10 alkynyl, (4) C1–10 alkoxy, (5) C1–10 alkylthio, (6) halogen atom, (7) trihalomethyl, (8) trihalomethoxy, (9) trihalomethylthio, (10) cyano, (11) nitrile, or (12) —$NR^6R^7$, $R^6$ and $R^7$ each independently represent C1–10 alkyl, m and n each independently represents 0 or integer of 1–3, or a nontoxic salt thereof, (2) a process for preparing thereof, and (3) an agent comprising thereof as an active ingredient.

In the formula (I), the C1–10 alkyl group includes methyl, ethyl, propyl, butyl, pentyl, hexyl, heptyl, octyl, nonyl, and decyl groups, and isomers thereof.

In the formula (I), the C2–10 alkenyl group includes ethenyl, propenyl, butenyl, pentenyl, hexenyl, heptenyl, octenyl, nonenyl, decenyl groups, and isomers thereof.

In the formula (I), the C2–10 alkynyl group includes ethynyl, propynyl, butynyl, pentynyl, hexynyl, octynyl, nonynyl, decynyl groups, and isomers thereof.

In the formula (I), the C1–10 alkoxy group includes methoxy, ethoxy, propoxy, butoxy, pentyloxy, hexyloxy, heeptyloxy, octyloxy, nonyloxy, decyloxy groups, and isomers thereof.

In the formula (I), the C1–10 alkylthio group includes methylthio, ethylthio, propylthio, butylthio, pentylthio, hexylthio, heptylthio, octylthio, nonylthio, and decylthio groups, and isomers thereof.

In the formula (I), the C1–3 alkylene group includes ethylene, ethylene, and trimethylene groups, and isomers thereof.

In the formula (I), the C1–4 alkylene group includes methylene, ethylene, trimethylene, and tetramethylene groups, and isomers thereof.

In the formula (I), the halogen atom means a chlorine, bromine, fluorine or iodine atom.

In the formula (I), the trihalomethyl group includes methyl group which is substituted by three halogen atoms.

In the formula (I), the trihalomethoxy group includes methoxy group which is substituted by three halogen atoms.

In the formula (I), the trihalomethylthio group includes methylthio group which is substituted by three halogen atoms.

In the formula (I), C3–7 cycloalkylene group, which is $R^2$ and $R^3$ taken together with the carbon atom to which they are attached includes cyclopropylene, cyclobutylene, cyclopentylene, cyclohexylene, and cycloheptylene groups.

In the formula (I), partially or fully optionally saturated C3–15 mono- or bi-carbocyclic aryl represented by Cyc1 and Cyc2, means, for example, cyclopropane, cyclobutane, cyclopentane, cyclohexane, cycloheptane, cyclooctane, cyclononane, cyclodecane, cycloundecane, cyclododecane, cyclotridecane, cyclopropene, cyclobutene, cyclopentene, cyclohexene, cycloheptene, cyclooctene, cyclopentadiene, cyclohexadiene, cycloheptadiene, cyclooctadiene, benzene, indene, naphthalene, indan, teterahydronaphthalene, bicyclo[3.3.0]octane, bicyclo[4.3.0]nonane, bicyclo[4.4.0]decane, spiro[4.4]nonane, spiro[4.5]decane, spiro[5.5]undecane, fluorene, anthracene, 9,10-dihydroanthracene, bicyclo[3.1.1]heptane, bicyclo[3.1.1]-2-heptene, adamantane, bicyclo[2.2.2]octane, acenaphthene, etc.

In the formula (I), among partially or fully optionally saturated 3–15 membered mono-, bi- or tri-heterocyclic aryl containing 1–4 hetero atom(s) selected from oxygen, nitrogen or sulfur atom represented by Cyc1 and Cyc2, 3–15 membered mono-, bi- or tri-heterocyclic aryl containing 1–4 hetero atom(s) selected from oxygen, nitrogen or sulfur atom means, for example, pyrrole, imidazole, triazole, tetrazole, pyrazole, pyridine, pyrazine, pyrimidine, pyridazine, azepine, diazepine, furan, pyran, oxepine, thiophene, thiaine (thiopyran), thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, benzofuran, isobenzofuran, benzothiophene, isobenzothiophene, indazole, quinoline, isoquinoline, phthalazine, naphthyridine, quinoxaline, quinazoline, cinnoline, benzoxazole, benzothiazole, benzimidazole, chromene, benzoxepine, benzoxazepine; benzoxadiazepine, benzothiepine, benzothiazepine, benzothiadiazepine, benzazepine, benzodiazepine, benzofurazan, benzothiadiazole, benzotriazole, carbazole, acridine, dibenzofuran, dibenzothiophene, phenothiazine, etc.

Also, partially or fully saturated 3–15 membered mono-, bi- or tri-heterocyclic aryl containing 1–4 hetero atom(s) selected from oxygen, nitrogen or sulfur atom, means, pyrroline, pyrrolidine, imidazoline, imidazolidine, pyrazoline, pyrazolidine, triazoline, triazolidine, tetrazoline, tetrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrothiophene, tetrahydrothiophene, dihydrothiaine (dihydrothiopyran), tetrahydrothiaine (tetrahydrothiopyran), dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrooxadiazole, tetrahydrooxadiazole (oxadiazolidine), dihydrothiadiazole, tetrahydrothiadiazole (thiadiazolidine), tetrahydrooxadiazine, tetrahydrothiadiazine, tetrahydrooxazepine, tetrahydrooxadiazepine, perhydrooxazepine, perhydrooxadiazepine, tetrahydrothiazepine, tetrahydrothiadiazepine, perhydrothiazepine, perhydrothiadiazepine, morpholine, thiomorpholine, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, dihydrobenzoxazole, perhydrobenzoxazole, dihydrobenzothiazole, perhydrobenzothiazole, dihydrobenzimidazole, perhydrobenzimidazole, dihydrocarbazole, tetrahydrocarbazole, perhydrocarbazole, dihydroacridine, tetrahydroacridine, perhydroacridine, dihydrodibenzofuran, dihydrodibenzothiophene, tetrahydrodibenzofuran, tetrahydrodibenzothiophene, perhydrodibenzofuran, perhydrodibenzothiophene, dioxolane, dioxane, dithiolane, dithiane, benzodioxarane, benzodioxane, 1,3-dioxaindan, chroman, benzodithiolane, benzodithiane; 8-aza-1,4-dioxaspiro[4,5]decane, 3-azaspiro [5.5]undecane, 1,3,8-triazaspiro[4.5]decane, etc.

In the formula (I), 1H-tetrazol-5-yl group means

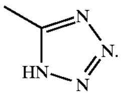

Unless otherwise specified, all isomers are included in the present invention. For example, alkyl, alkoxy and alkylene group includes straight or branched ones. In addition, isomers on double bond, ring, fused ring (E-, Z-, cis-, trans-isomer), isomers generated from asymmetric carbon atom(s) (R-, S-, α-, β-isomer, enantiomer, diastereomer), optically active isomers (D-, L-, d-, 1-isomer), polar compounds generated by chromatographic separation (more polar compound, less polar compound), equilibrium compounds, rotamer, mixtures thereof at voluntary ratios and racemic mixtures are also included in the present invention.

According to the present invention, unless otherwise indicated and as is apparent for those skilled in the art, symbol  indicates that it is bound to the opposite side of the sheet (namely α-configuration), symbol  indicates that it is bound to the front side of the sheet (namely β-configuration), symbol  indicates that it is α-, β- or a mixture thereof, and symbol 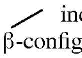 indicates that it is a mixture of α-configuration and β-configuration.

The compound of the present invention can be converted into a nontoxic salt by known methods. A nontoxic salt is preferably pharmaceutically acceptable and water-soluble.

A nontoxic salt means, for example, salts of alkali metals (e.g., potassium, sodium, lithium, etc.), salts of alkaline earth metals (e.g., calcium, magnesium, etc.), ammonium salts (e.g., tetramethylammonium, tetrabutylammonium, etc.), salts of organic amines (e.g., triethylamine, methylamine, dimethylamine, cyclopentylamine, benzylamine, phenethylamine, piperidine, monoethanolamine, diethanolamine, tris(hydroxymethyl) methylamine, lysine, arginine, N-methyl-D-glucamine, etc.), acid-addition salts (e.g., inorganic acid salts (e.g., hydrochloride, hydrobromate, hydroiodate, sulfate, phosphate, and nitrate, etc.), organic acid salts (e.g., acetate, trifluoroacetate, lactate, tartrate, oxalate, fumarate, maleate, benzoate, citrate, methane sulfonate, ethane sulfonate, benzene sulfonate, toluene sulfonate, isethionate, glucuronate, gluconate, etc.), etc.

Furthermore, a solvate of compound of the present invention represented by formula (I), and the above alkali (earth) metals, ammonium, organic amines and acid-addition salts thereof, is included in the present invention.

The solvate is preferably nontoxic and water-soluble. Appropriate solvates means, for example, solvates such as water, an alcohol solvent (e.g.; ethanol, etc.), etc.

In the present invention, PPAR regulator includes all the regulators of PPAR α, γ, δ, α+γ, α+δ, γ+δ and α+γ+δ. Preferable regulatory fashion is, PPAR α regulator, PPAR γ regulator, PPAR δ regulator, PPAR α+γ regulator, PPAR α+δ regulator, more preferably PPAR α+γ regulator. PPAR regulator also includes PPAR agonist and PPAR antagonist, preferably PPAR agonist, more preferably PPAR α agonist, PPAR γ agonist, PPAR δ agonist, PPAR α+γ agonist or PPAR α+δ agonist, particularly preferably PPAR α+γ agonist.

In the formula (I), A is preferably —$COOR^1$.

In the formula (I), $R^2$ and $R^3$ are preferably hydrogen atom or C1–4 alkyl, and more preferably hydrogen atom or methyl group.

In the formula (I), X is preferably C1–3 alkylene group, and more preferably C1 alkylene group (—$CH_2$—).

In the formula (I), Y is preferably —O— group or —S— group, and more preferably —O— group.

In the formula (I),

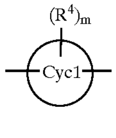

is preferably

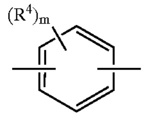 , 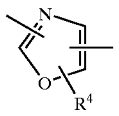 , or 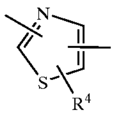 , more preferably

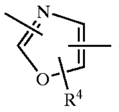 .

Among the compounds represented by formula (I), preferred compounds are compounds represented by formula (I-A)

(I-A)

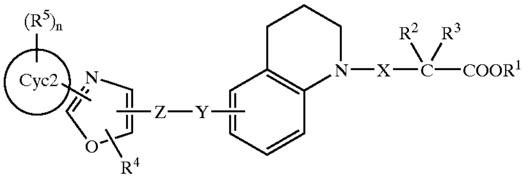

(wherein all symbols have the same meanings as described above.); compounds represented by formula (I-B)

(I-B)

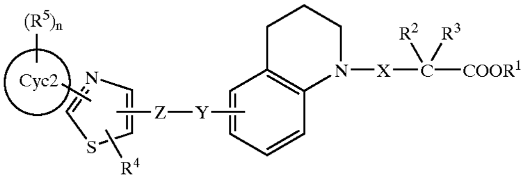

(wherein all symbols have the same meanings as described above.), and compounds represented by formula (I-C)

(I-C)

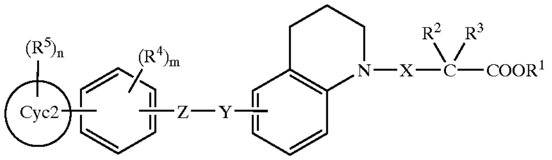

(wherein all symbols have the same meanings as described above.).

Concrete compounds of the present invention include compounds shown in Tables 1 to 3, compounds described in Examples, and nontoxic salts thereof.

In each Table, Me represents methyl group, Et represents ethyl group, Pr represents propyl group, t-Bu represents tertiarybutyl group, and other symbols have the same meanings as described above.

TABLE 1

(I-A-1)

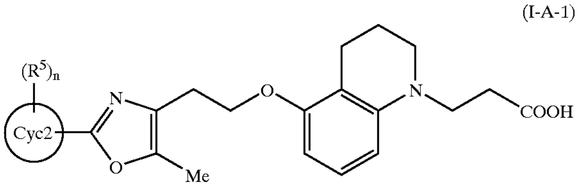

| No. | 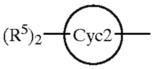 |
|---|---|
| 1 | 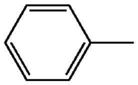 |
| 2 | 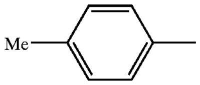 |
| 3 | 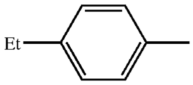 |
| 4 | 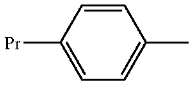 |
| 5 | 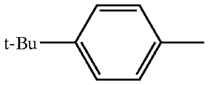 |
| 6 | 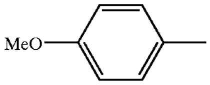 |
| 7 | 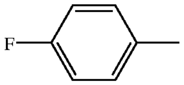 |
| 8 | 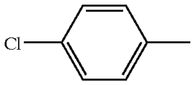 |

TABLE 1-continued (I-A-1)

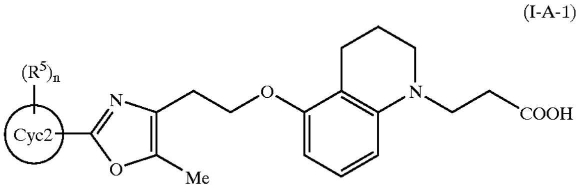

| No. | 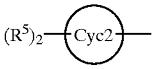 |
|---|---|
| 9 | 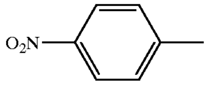 |
| 10 | 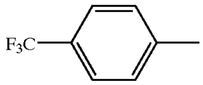 |
| 11 | 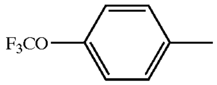 |
| 12 | 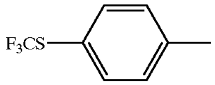 |
| 13 | 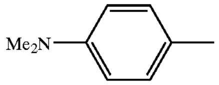 |
| 14 | 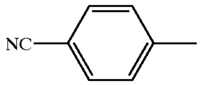 |
| 15 | 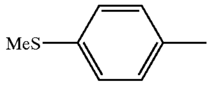 |
| 16 | 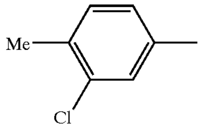 |
| 17 | 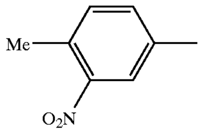 |
| 18 | 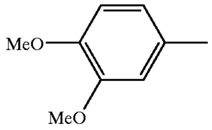 |
| 19 | 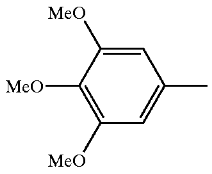 |

TABLE 1-continued
(I-A-1)
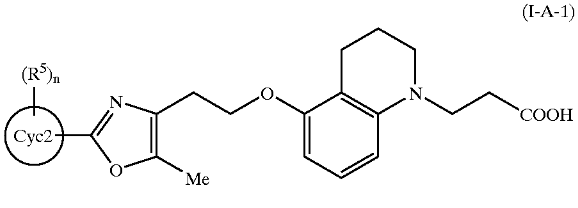
| No. | 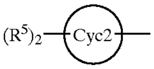 |
|---|---|
| 20 | 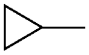 |
| 21 | 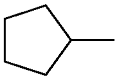 |
| 22 | 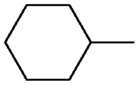 |
| 23 | 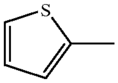 |
| 24 | 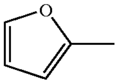 |
| 25 | 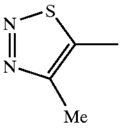 |
| 26 | 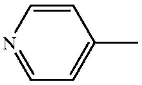 |
| 27 | 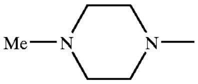 |
| 28 | 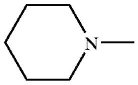 |
| 29 | 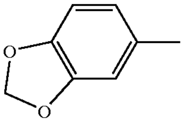 |
| 30 | 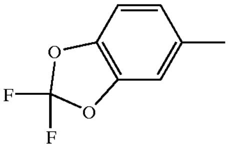 |
TABLE 2
(I-B-1)
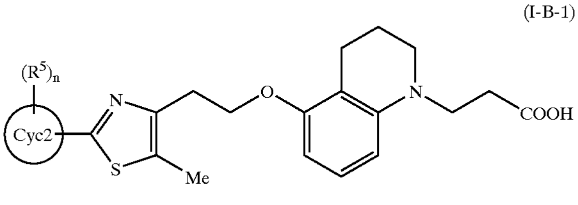
| No. | 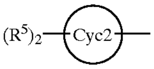 |
|---|---|
| 1 | 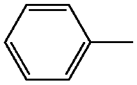 |
| 2 | 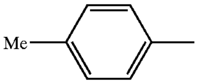 |
| 3 | 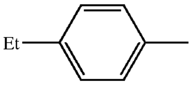 |
| 4 | 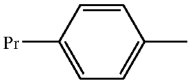 |
| 5 | 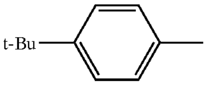 |
| 6 | 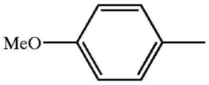 |
| 7 | 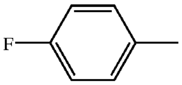 |
| 8 | 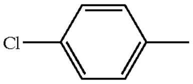 |
| 9 | 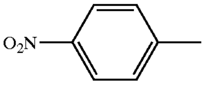 |
| 10 | 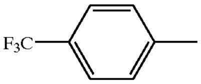 |
| 11 | 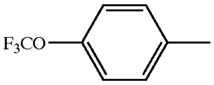 |
| 12 | 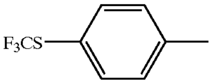 |
| 13 | 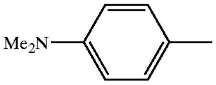 |

TABLE 2-continued
(I-B-1)
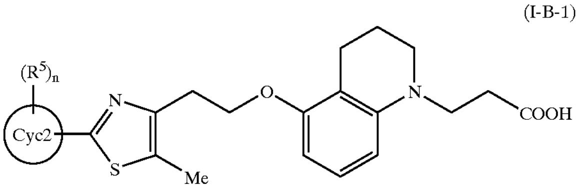
| No. | 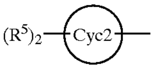 |
|---|---|
| 14 | 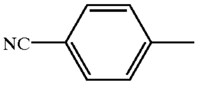 |
| 15 | 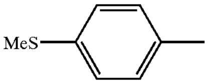 |
| 16 | 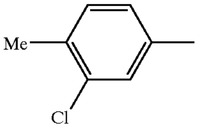 |
| 17 | 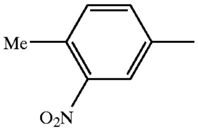 |
| 18 | 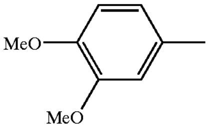 |
| 19 | 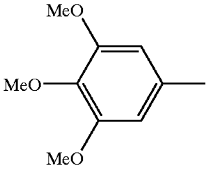 |
| 20 | 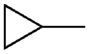 |
| 21 | 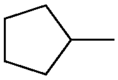 |
| 22 | 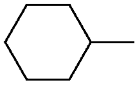 |
| 23 | 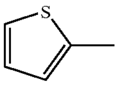 |
| 24 | 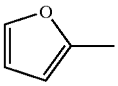 |
TABLE 2-continued
(I-B-1)
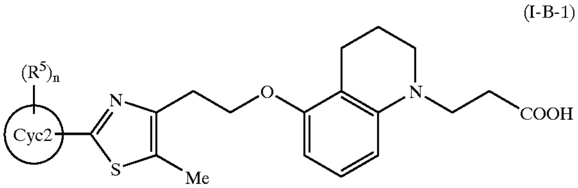
| No. | 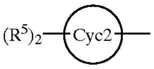 |
|---|---|
| 25 | 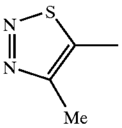 |
| 26 | 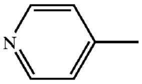 |
| 27 | 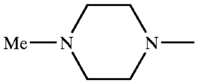 |
| 28 | 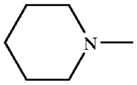 |
| 29 | 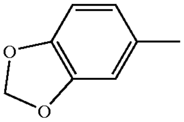 |
| 30 | 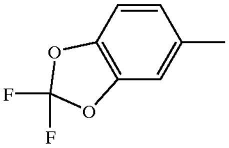 |
TABLE 3
(I-C-1)
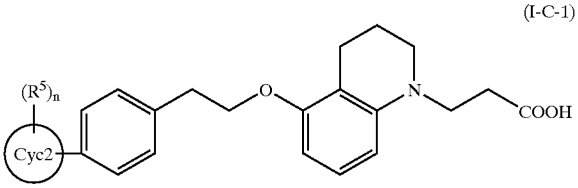
| No. | 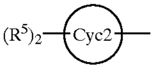 |
|---|---|
| 1 | 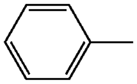 |
| 2 | 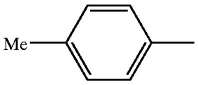 |

TABLE 3-continued
(I-C-1)
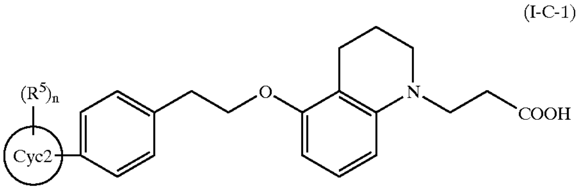
| No. | 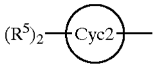 |
| --- | --- |
| 3 | 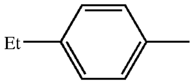 |
| 4 | 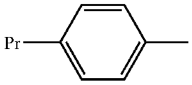 |
| 5 | 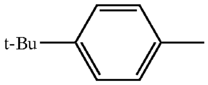 |
| 6 | 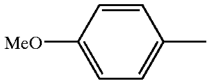 |
| 7 | 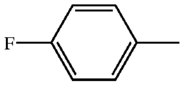 |
| 8 | 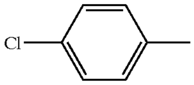 |
| 9 | 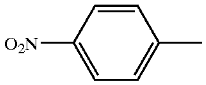 |
| 10 | 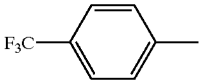 |
| 11 | 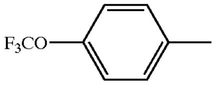 |
| 12 | 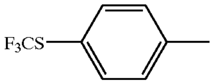 |
| 13 | 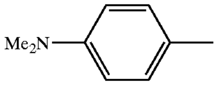 |
| 14 | 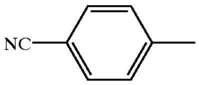 |
| 15 | 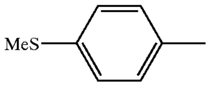 |
TABLE 3-continued
(I-C-1)
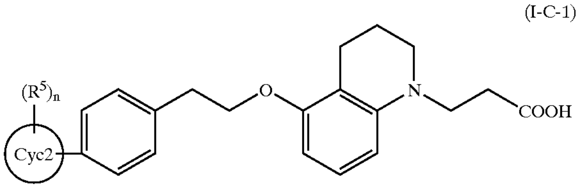
| No. | 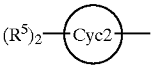 |
| --- | --- |
| 16 | 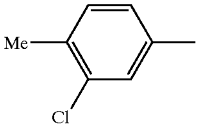 |
| 17 | 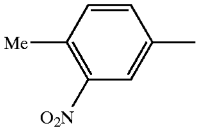 |
| 18 | 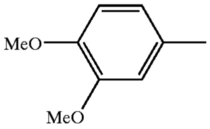 |
| 19 | 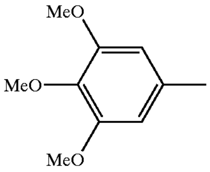 |
| 20 | 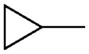 |
| 21 | 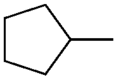 |
| 22 | 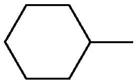 |
| 23 | 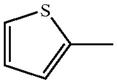 |
| 24 | 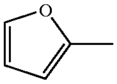 |
| 25 | 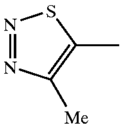 |
| 26 | 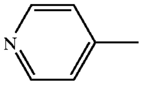 |

TABLE 3-continued (I-C-1)

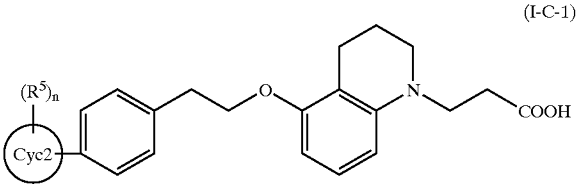

| No. | 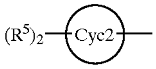 |
|---|---|
| 27 | 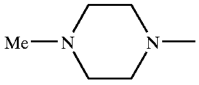 |
| 28 | 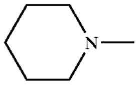 |
| 29 | 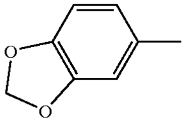 |
| 30 | 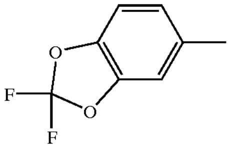 |

Processes for the Preparation of the Compound of the Present Invention:

(1) Among the compounds of the present invention represented by formula (I), a compound in which A represents a $COOR^1$ group, and $R^1$ represents C1–10 alkyl group, i.e., a compound represented by formula (IA)

(IA)

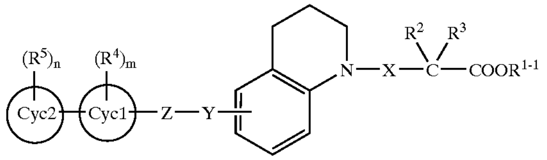

(wherein $R^{1-1}$ represents C1–10 alkyl group, and other symbols have the same meanings as described above.) can be prepared by reacting a compound represented by formula (II)

(II)

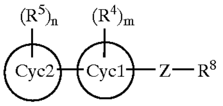

(wherein $R^8$ is represents a leaving group (e.g., a halogen atom, a mesyloxy group or a tosyloxy group, etc.), and other symbols have the same meanings as described above.) with a compound represented by formula (III)

(III)

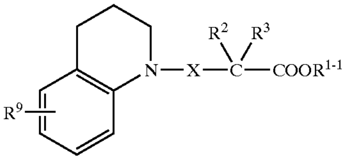

(wherein $R^9$ represents OH group or SH group, and other symbols have the same meanings as described above.).

This reaction is known. For example, it is carried out at 0 to 80° C. in an organic solvent (e.g., tetrahydrofuran (THF), diethyl ether, methylene chloride, chloroform, carbon tetrachloride, pentane, hexane, benzene, toluene, dimethylformamide (DMF), dimethylsulfoxide (DMSO), hexamethylphosphoramide (HMPA), etc.) in the presence of a base (e.g., sodium hydride, potassium carbonate, triethylamine, pyridine, sodium iodide, cesium carbonate, etc.).

Furthermore, among the compounds represented by formula (IA), a compound in which Y represents —O— group, i.e., a compound represented by formula (IA-1)

(IA-1)

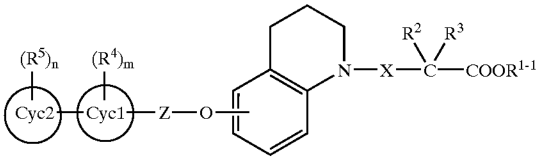

(wherein all symbols have the same meanings as described above.) can be prepared by reacting a compound represented by formula (IV)

(IV)

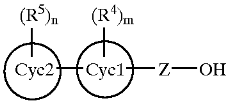

(wherein all symbols have the same meanings as described above.) with a compound represented by formula (III-1)

(III-1)

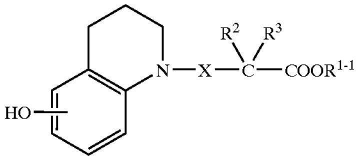

(wherein all symbols have the same meanings as described above.).

This reaction is known. For example, it is carried out at 0 to 60° C. by reacting with a corresponding alcohol compound in an organic solvent (e.g., dichloromethane, diethyl ether, tetrahydrofuran, acetonitrile, benzene, toluene, etc.) in the presence of an azo compound (e.g., diethyl azodicarboxylate, diisopropyl azodicarboxylate, 1,1'-(azodicarbonyl)dipiperidine, 1,1'-azobis(N,N-dimethylformamide), etc.) and a phosphine compound (e.g., triphenylphosphine, tributylphosphine, trimethylphosphine, etc.).

(2) Among the compounds represented by formula (I), a compound in which A represents $COOR^1$ group, and $R^1$ represents hydrogen atom, i.e., a compound represented by formula (IB)

(IB)

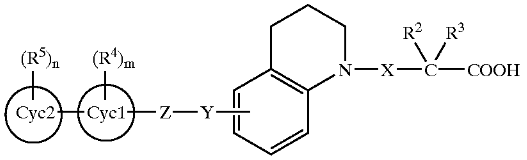

(wherein all symbols have the same meanings as described above.) can be prepared by subjecting the above compound represented by formula (IA) to a hydrolysis reaction.

The said hydrolysis reaction is known. It is carried out, for example, (1) in an organic solvent admissible with water (e.g., THF, dioxane, ethanol, methanol, propanol etc.) or mixture solvent thereof, using an aqueous solution of alkali (e.g., potassium hydroxide, sodium hydroxide, lithium hydroxide, potassium carbonate, sodium carbonate etc.), or (2) in alkanol (e.g., methanol, ethanol etc.), using the above alkali under an anhydrous condition. These reactions may be carried out at 0 to 100° C. normally.

Also, among the compounds represented by formula (IB) can be prepared by subjecting a compound of formula (V)

(V)

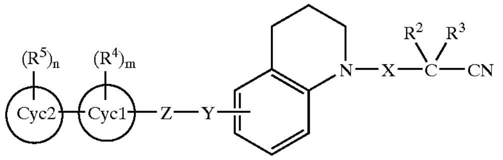

(wherein all symbols have the same meanings as described above.) to a hydrolysis reaction.

This hydrolysis reaction is known. It is carried out, for example, in an organic solvent admissible with water (e.g., tetrahydrofuran, dioxane, ethanol, methanol, propanol, etc.) using an aqueous solution of alkali (e.g., potassium hydroxide, sodium hydroxide, lithium hydroxide, potassium carbonate, sodium carbonate, etc.) at room temperature to reflux temperature.

(3) Among the compounds represented by formula (I), a compound in which A represents 1H-tetrazol-5-yl group, i.e., a compound represented by formula (IC)

(IC)

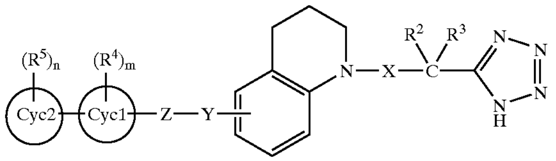

(wherein all symbols have the same meanings as described above.) can be prepared by subjecting the compound represented by formula (V) to a cyclization reaction.

This cyclization reaction is known. For example, it is carried out at 0° C. to reflux temperature in an organic solvent (e.g., toluene, benzene, tetrahydrofuran, chloroform, methyene chloride, diethylether, etc.) using an azido reagent (e.g., trimethylsilyl azide, sodium azide, azidotrimethylthin, copper azide, etc.).

The compounds represented by formulae (II), (III), (IV) and (V) are known compounds or can be prepared easily by known methods or methods described in Examples.

For example, among the compounds of formula (IV), 2-(5-methyl-2-phenyloxazol-4-yl)ethanol can be prepared by the methods described in J. Med. Chem., 35, 1853–1864 (1992).

For example, among the compounds of formula (IV), 2-(5-methyl-2-(morpholin-4-yl)oxazol-4-yl)ethanol can be prepared by the methods described in J. Med. Chem., 41, 5037–5054 (1998).

For example, the compounds represented by formulae (III) and (V) can be prepared by the methods shown by the following Reaction Schemes 1 to 2.

In the reaction schemes, $R^{10}$ represents a protecting group of hydroxy group (e.g., methyl group, trityl group, methoxyethyl (MOM) group, 1-ethoxyethyl (EE) group, methoxyethoxymethyl (MEM) group, 2-tetrahydropyranyl (THP) group, trimethylsilyl (TMS) group, triethylsilyl (TES) group, t-butyldimethylsilyl (TBDMS) group, acetyl (Ac) group, pivaloyl group, benzoyl group, benzyl (Bn) group, p-methoxybenzyl group, allyloxycarbonyl (Alloc) group, 2,2,2-trichloroethoxycarbonyl (Troc) group etc.), halo represents halogen atom, $X^1$ represents bond or C1–2 alkylene group, and other symbols have the same meanings as described above.

Reaction Scheme 1
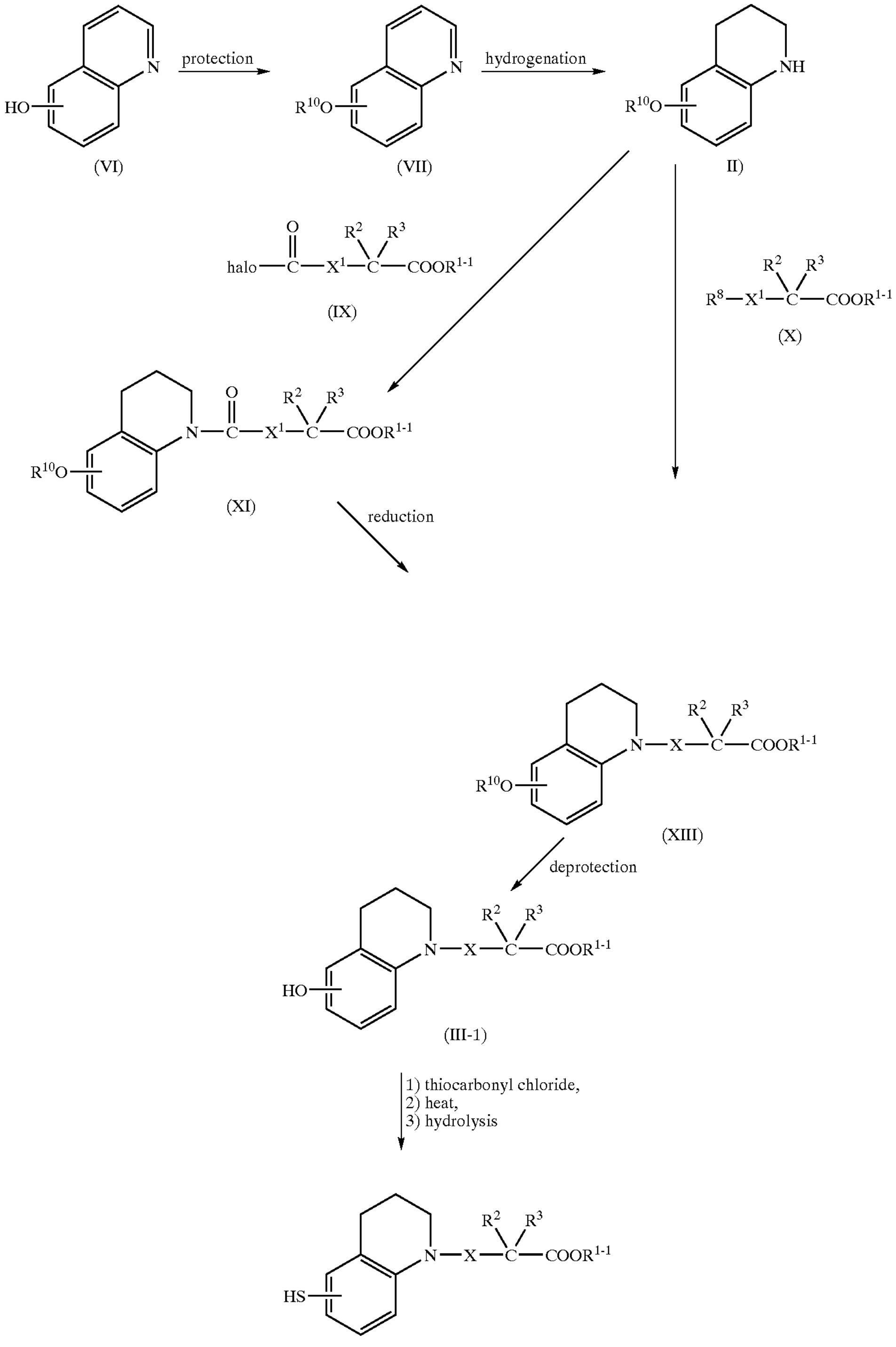
(VI) (VII) II) (IX) (X) (XI) (XIII) (III-1) (III-2)

Reaction Scheme 2

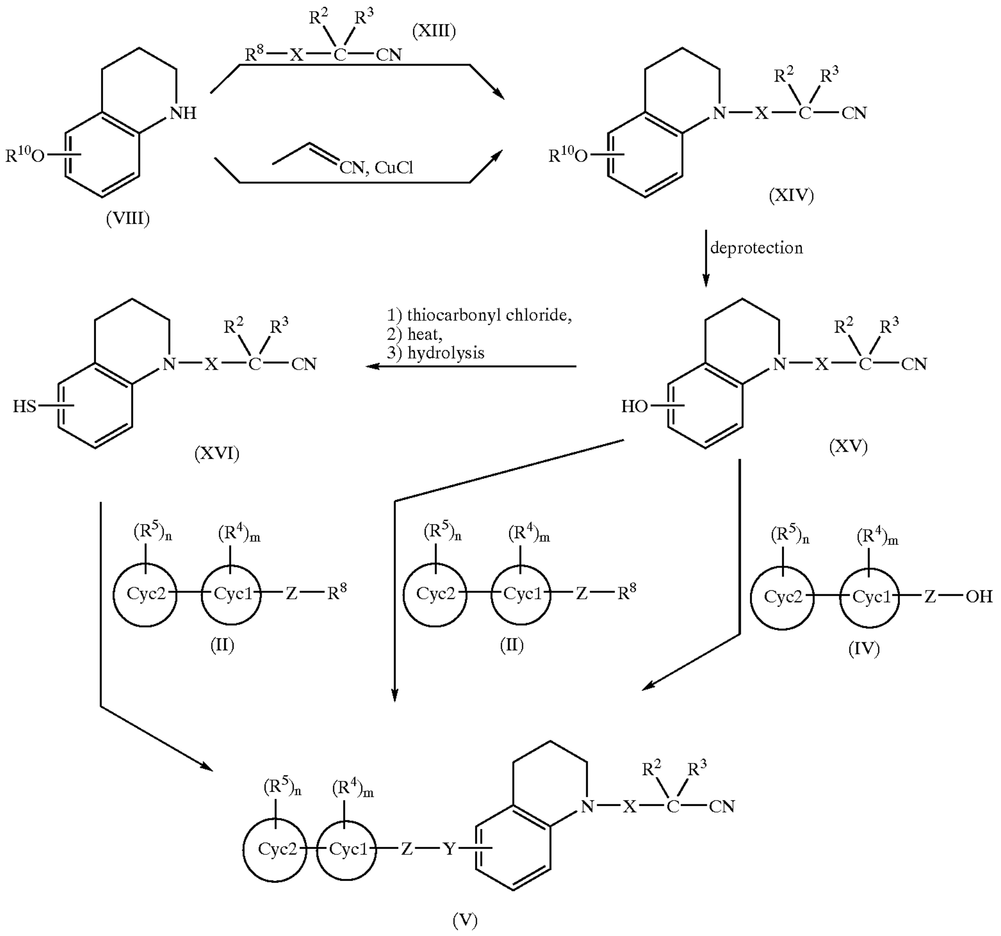

In Reaction Scheme 1, the compounds to be used as the starting materials represented by formulae (VI), (IX), (X) and (XIII) are known compounds or can be prepared easily by known methods.

In each reaction described herein, the reaction product can be purified by general purification techniques such as distillation under ordinary pressure or a reduced pressure, high performance liquid chromatography, thin layer chromatography or column chromatography using silica gel or magnesium silicate, washing and recrystallization. Purification may be carried out in each reaction or after completion of several reactions.

Pharmacological Activity:

It was confirmed that compounds of the present invention of formula (I) has PPAR regulating activities by the following experiments.

Measurement of PPAR α Agonistic and PPAR γ Agonistic Activities (1) Preparation of Materials in Luciferase Assay Using Human PPAR α or γ

The whole operations were carried out by the basic methods in gene engineering techniques and the conventional methods in yeast One-hybrid or Two-hybrid system.

As a luciferase gene expression vector under the control of thymidine kinase (TK) promotor, luciferase structural gene was excised from PicaGene Basic Vector 2 (trade name, Toyo Ink Inc., catalogue No. 309-04821), to prepare luciferase gene expression vector pTK-Luc. under the control of TK promotor (−105/+51) as a minimum essential promotor activity from pTK□ having TK promotor (Chrontech Inc., catalogue No. 6179-1). In the upper stream of TK promotor, four times repeated UAS sequence was inserted, which is the response element of Gal4 protein, a basic transcription factor in yeast, to construct 4×UAS-TK-Luc. as reporter gene. The following is the enhancer sequence used (Sequence No. 1).

Sequence No. 1: Enhancer sequence repeating Gal4 response element four-times tandemly.

5'-T(CGACGGAGTACTGTCCTCCG)×4 AGCT-3'

A vector was prepared as described hereafter which expresses chimeric receptor protein wherein in carboxy terminus of yeast Gal4 protein DNA binding domain was fused to ligand binding domain of human PPAR α or γ. That is to say, PicaGene Basic Vector 2 (trade name, Toyo Ink Inc., catalogue No. 309-04821) was used as a basic expression vector, the structural gene was exchanged for that of chimeric receptor protein, while promotor and enhancer domains were kept as they were.

DNA encoding a fused protein composed of Gal4 DNA binding domain, the 1st to 147th amino acid sequence linked to the ligand binding domain of human PPAR α or γ in frame was inserted to the downstream of promotor/enhancer in PicaGene Basic Vector 2 (trade name, Toyo Ink Inc., catalogue No. 309-04821). Here the DNA was aligned as follows; in the amino terminus of human PPAR α or γ ligand binding domain, nuclear translocation signal originated from SV-40 T-antigen, Ala Pro Lys Lys Lys Arg Lys Val Gly (sequence No. 2) was added to make fusion protein localizing intranuclearly. On the other hand, in the carboxy terminus of them, influenza hemagglutinin epitope, Tyr Pro Tyr Asp Val Pro Asp Tyr Ala (sequence No. 3) and stop codon for translation was added in this order, to detect an expressed fused protein tagged epitope sequence.

According to the comparison of human PPAR structures described in the literatures by R. Mukherjee et al. (See J. Steroid Biochem. Molec. Biol., 51, 157 (1994)), M. E. Green et al., (See Gene Expression., 4, 281 (1995)), A. Elbrecht et al. (See Biochem Biophys. Res. Commun., 224, 431 (1996)) or A. Schmidt et al. (See Mol. Endocrinology., 6, 1634 (1992)), the portion of structural gene used as ligand binding domain of human PPAR α or γ was DNA encoding the following peptide:

human PPAR α ligand binding domain: $Ser^{167}$-$Tyr^{468}$
human PPAR γ ligand binding domain: $Ser^{176}$-$Tyr^{478}$
(each human PPAR γ1 ligand binding domain and human PPAR γ2 ligand binding domain is $Ser^{204}$–$Tyr^{506}$ which is identical sequence each other).

In order to measure basal level of transcription, an expression vector containing DNA binding domain of Gal4 protein lacking in PPAR ligand binding domain, which is exclusively encoding the 1st to 147th amino acid sequence in Gal4 protein was also prepared.

(2) Luciferase Assay Using Human PPAR α or γ

CV-1 cells used as host cells were cultured by a conventional technique. That is to say, Dulbecco's modified Eagle medium (DMEM) supplemented 10% bovine fetal serum (GIBCO BRL Inc., catalogue No. 26140-061) and 50 U/ml of penicillin G and 50 μg/ml of streptomycin sulfate were used to culture CV-1 cells under the atmosphere of 5% carbon dioxide gas at 37° C.

$2\times10^6$ cells were seeded in a 10 cm dish, and once washed with the medium without serum, followed by addition of the medium (10 ml) thereto. Reporter gene (10 μg), Gal4-PPAR expression vector (0.5 μg) and 50 μl of LipofectAMINE (GIBRO BRL Inc., catalogue No. 18324-012) were well mixed and added to the culture to introduce these DNAs into the host cells. They were cultured at 37° C. for 5 to 6 hours, and thereto was added 10 ml of medium containing 20% of dialyzed bovine fetal serum (GIBRO BRL Inc., catalogue No. 26300-061), and then cultured at 37° C. overnight. The cells were dispersed by trypsin, and they were again seeded in 96-well plates in a density of 8000 cells/100 ml of DMEM-10% dialyzed serum/well. Several hours after the cultivation, when cells were attached to the plastic ware, then 100 μl of DMEM-10% dialyzed serum containing the compounds of the present invention, whose concentration is twice as high as the final concentration of them, was added thereto. The culture was settled at 37° C. for 42 hours and the cells were dissolved to measure luciferase activity according to manufacturer's instruction.

As to PPAR α agonistic activity, the relative activity of the compounds of the present invention (10 μM) was shown in Table 4, under the condition that luciferase activity was defined as 1.0 in case of carbacyclin (10 μM) as a positive control compound, which could activate transcription of luciferase gene significantly to PPAR α (See Eur. J. Biochem., 233, 242 (1996); Genes & Development., 10, 974 (1996)).

As to PPAR γ agonistic activity, the relative activity of the compounds of the present invention (10 μM) was shown in Table 5, under the condition that luciferase activity was defined as 1.0 in case of troglitazone (10 μM) as a positive control compound, which could activate transcription of luciferase gene significantly to PPAR γ (See Cell., 83, 863 (1995); Endocrinology., 137, 4189 (1996) and J. Med. Chem., 39, 665 (1996)) and has been already launched as hypoglycemic agent.

Furthermore, assay of each compound was carried out three times to examine its reproducibility and to confirm the dose dependent activity.

TABLE 4

| Compound No. | Relative Activity to a positive control compound (carbacyclin = 1) |
|---|---|
| Example 2 | 0.5 |

TABLE 5

| Compound No. | Relative Activity to a positive control compound (troglitazone = 1) |
|---|---|
| Example 2 | 6.7 |

For example, Hypoglycemic and hypolipidemic effects of the compounds of the present invention can be measured by the following methods.

Hypoglycemic and Hypolipidemic Effects (1):

Male, 8-weeks old KKAy/Ta Jcl mice (five mice per group) are pre-breaded individually in single cages for approximately one week and provided pellet diet and tap water from bottle of feed water ad libitum. Mice are acclimatized to switch over to milled diet for three days. On the first day of the experiment (Day 0), the body weight of mice are measured. Blood samples are collected from coccygeal vein using a microcapillary to measure plasma glucose concentration. Based on plasma glucose concentration, mice are divided into some groups (five mice per group) using a stratified randomization method. The body weight of mice are measured on the morning of the next day, and from the next day for six days they are given compounds by food mixture containing 0.03% (w/w), 0.01% (w/w) or 0.003% (w/w) of the compound of the present invention or by milled diet only. On the morning of the fourth and the seventh day, body weights and food intakes of them are determined to calculate the mean administered dose. On the morning of the sixth day, blood samples were collected from coccygeal vein to measure glucose and triglyceride (TG) levels. On the seventh day after measuring body weight, blood samples are collected from abdominal vena cava under anesthetized condition by ether to determine plasma insulin, non-esterified fatty acid (NEFA), GOT and GPT levels using commercially available kits. And, the liver is removed and weighed. The total RNAs are prepared from left lobe of the liver and measured a gene expression level of bi-functional protein (hydrase-dehydrogenase, HD) by Northern blot method. Actually, there is no significant difference in the food intake between control group (milled diet only) and compounds-treated group (milled diet containing 0.03%, 0.01% or 0.003% of compounds). The calculated dose is approximately 40 mg/kg/day in the group given diet containing 0.03% of the compound.

It is suggested the possibility as an agent for preventing and/or treating of diabetes mellitus, hyperlipidemia, atherosclerosis etc., from ameliorating effects of plasma glucose, plasma insulin, NEFA or TG levels in well-fed KKAy/Ta mice. This effect is likely to be mediated through PPAR γ activation in vivo. Additionally, it is likely that an increase in liver weight and in an expression of HD mRNA depends on PPAR α activation in vivo.

Hypoglycemic and Hypolipidemic Effects (2):

Male, 8-weeks old Zucker fa/fa rats (Strain: Crj-[ZUC]-fa/fa) and healthy Zucker lean rats (Strain: Crj-[ZUC]-lean) to be contrasted are pre-breaded individually in single cages for approximately two weeks and provided pellet diet and tap water from automatic water supplying equipment ad libitum. For five days before the treatment, rats are acclimatized to oral gavage administration. During this period, a general condition of them is observed, and healthy rats with 10-weeks of age are used for experiment. The body weight of each rats are measured on the morning of the first day of experiment (Day 0) and blood samples are collected from coccygeal vein using a microcapillary to measure plasma glucose, TG, NEFA concentrations and HbA1c. Based on the HbA1c and body weight, rats are assigned to groups comprised of five animals each using a stratified randomization method. Additionally, rats are interchanged optionally to prevent the deflection of other parameters' averages between groups. The body weight of each animal was measured every morning from the day after grouping. Volumes to be administered are calculated on the basis of body weight measured on the day of administration, and oral gavage administration of compound of the present invention or vehicle only (0.5% methylcellulose) is conducted once a day for 13 days. The healthy animals (lean rats) are given vehicle only.

Food consumption is measured on the morning of Day 1, 4, 7, 10 and 13 to calculate mean food intakes. On the seventh day, blood samples are corrected from coccygeal vein using microcapillary to measure plasma glucose, TG, NEFA concentrations and HbA1c. And on the 14th day, oral glucose tolerance test (OGTT) is performed to evaluate improving effect on glucose intolerance. Rats are fasted on the previous day (Day 13) to perform OGTT. After blood samples are collected on the next day (Day 14), 40% glucose solution is loaded at a volume of 2 g/5 ml/kg per oral administration. 60 and 120 minutes after loading, blood samples are collected from coccygeal vein using microcapillary to determine plasma glucose levels.

Animals are given food after the OGTT and administered compound of the present invention on Day 15. On the morning of the 16th day after measuring body weight, blood samples are collected from abdominal vena cava under anesthetized condition by ether to determine plasma glucose, plasma insulin, TG, NEFA, GOT and GPT levels. And, the liver is removed and weighed.

It is suggested the possibility as an agent for preventing and/or treating of diabetes mellitus, hyperlipidemia, atherosclerosis etc., from ameliorating effects of plasma glucose, plasma insulin, TG, NEFA levels or HbA1c in well-fed Zucker fa/fa rats. Also, a decrease effect of fasting plasma glucose and improving effect of glucose intolerance during OGTT suggest the possibility as an agent for preventing and/or treating of diabetes mellitus. These effects are likely to be mediated through PPAR γ activation in vivo. Additionally, it is suggested that an increase in liver weight depends on PPAR α activation in vivo.

Hypoglycemic and Hypolipidemic Effects (3):

Male, 3- to 4-years old cynomolgus monkeys (Mean body weight: approximately 3 kg) to have a regal medical inspection are performed a medical inspection and acclimatized to be provided approximately 100 g of pellet diet once a day and tap water from automatic water supplying equipment ad libitum, individually in single monkey cages for more than one month. After then, animals become to take a diet within one hour. Additionally, animals are pre-breaded for 14 days. 14 and 7 days before the treatment, the body weight are measured, and then blood samples are collected from hindlimb saphenous vein to measure hematological (red blood cells, hematocrit, hemoglobin, platelet and leukocytes) and biochemical (GOT, GPT, alkaline phosphatase, total protein, blood urea nitrogen, creatinine, creatinine kinase, total bilirubin, glucose, total cholesterol, HDL, LDL and TG) parameters. Additionally, a general condition of animals is observed during acclimatizing and pre-breeding, and healthy animals are used for experiment. Also, food consumption is measured everyday.

On the basis of body weight measured on the final day of acclimatizing period, animals are divided into some groups (three animals per group) using a stratified randomization method. On the morning of Day 1, 3, 7, 10 and 14, body weight is measured. Volumes to be administered are calculated based on the latest body weight, and oral gavage administration with compound of the present invention (3–100 mg/kg/day) or vehicle alone (diluted solution) is conducted once a day for 14 days. 1, 7 and 14 days after the treatment, blood samples are collected to measure the above mentioned hematological and biochemical parameters before the administration of the compound of the present invention. It confirms that blood glucose is not changed with the compound of the present invention. Three weeks before, and 14 days after the start of treatment, blood samples are collected from hindlimb saphenous vein or antebrachial vein at 1, 2 and 4 hours after oral gavage, and also at 1, 2 and 3 hours after providing a diet, to measure plasma glucose and TG.

It is suggested the possibility as an agent for preventing and/or treating of hyperlipidemia and atherosclerosis etc., from ameliorating effects of plasma TG levels in fasted monkeys. These effects are likely to be mediated through PPAR α activation in vivo. It is also observed in suppressing effect on post-prandial TG increase. Additionally, it can be estimated whether compound have a toxicity risk from other biochemical parameters.

Toxicity:

The toxicity of the compound represented by formula (I) of the present invention is very low so that it is considered that the compound is sufficiently safe for using as a pharmaceutical.

INDUSTRIAL APPLICABILITY

Application to Pharmaceutical:

Since the compound represented by formula (I) of the present invention and nontoxic salt thereof have a PPAR modulating activity, it is expected to be applied as hypoglycemic agents, hypolipidemic agents, agents for preventing and/or treating of diseases associated with metabolic disorders such as diabetes, obesity, syndrome X, hypercholesterolemia and hyperlipoproteinemia etc., hyperlipidemia, atherosclerosis, hypertension, circulatory diseases, overeating, coronary heart diseases etc., HDL cholesterol-elevating agents, LDL cholesterol and/or VLDL cholesterol-lowering agents and agents for relieving risk factors of diabetes or syndrome X.

Also, since the compound represented by formula (I) of the present invention, and non-toxic salts thereof, have a PPARα agonist and/or PPAR γ agonist effect, it is expected to be applied as hypoglycemic agents, hypolipidemic agents, agents for preventing and/or treating of diseases associated with metabolic disorders such as diabetes, obesity, syndrome X, hypercholesterolemia, hyperlipoproteinemia etc., hyperlipidemia, atherosclerosis, hypertension, circulatory diseases and overeating etc., HDL cholesterol-elevating effect, LDL cholesterol and/or VLDL cholesterol-lowering effect, inhibition of progress of atherosclerosis and its treatment, and inhibitory effect against obesity. They are also expected to be useful for the treatment and/or prevention of diabetes as hypoglycemic agents for the amelioration of hypertension, for the relief from risk factors of syndrome X, and as agents for preventing against occurrence of coronary heart diseases.

In the present invention, the compound represented by formula (I) may be administered in combination with other drugs for the purpose of 1) complement and/or enhancement of preventing and/or treating effect, 2) improvement of dynamics and absorption of the compound, and lowering of dose, and/or 3) alleviation of side effect of the compound.

The compound represented by formula (I) may be administered in combination with other drugs as a composition in one drug product comprising these components, or may be administered separately. When they are administered independently, they may be administered simultaneously or with time lag. Administering with time lag includes the method of administering the compound represented by formula (I) before other drugs and vice versa; they may be administered in the same route or not.

The above combination takes effects on whichever disease treating and/or preventing effect of the compound represented by formula (I) is complemented and/or enhanced.

As other drugs to complement and/or to enhance hypolipidemic effect of the compound represented by the formula (I), for example, MTP (Microsomal Triglyceride Transfer Protein) inhibitor, HMG-CoA reductase inhibitor, squalene synthetase inhibitor, fibrate preparation (fibrinic acid derivatives), ACAT (acylCoA:cholesterol acyltransferase) inhibitor, 5-lipoxygenase inhibitor, cholesterol absorption inhibitor, bile acid absorption inhibitor, ileal $Na^+$/bile acid transporter (BAT) inhibitor, LDL receptor activator/up-regulator, lipase inhibitor, probcol preparation, nicotinic acid preparation, or other therapeutic agent for hypercholesterolemia, etc. are given.

As MTP inhibitor, for example, BMS-201038, BMS-212122, BMS-200150, GW-328713 and R-103757, etc. are given.

As HMG-CoA reductase inhibitor, for example, atorvastatin, fluvastatin, lovastatin, pitavastatin, pravastatin, rosuvastatin and simvastatin, etc. are given.

As ACAT inhibitor, for example, F-12511, F-1394 and CI-1011, etc. are given.

As squalene synthetase inhibitor, for example, TAK-475, etc. are given.

As fibrate preparation, for example, gemfibrozil, clofibaret, bezafibrate and fenofibrate, etc. are given.

As ACAT inhibitor, for example, CI-1011, FCE27677 and RP73163, etc. are given.

As cholesterol absorption inhibitor, for example, SCH48461, etc. are given.

As bile acid absorption inhibitor, for example, cholestyramine and cholestagel, etc. are given.

As LDL receptor activator/up-regulator, for example, MD-700 and LY295427, etc. are given.

As lipase inhibitor, for example, orlistat, etc. are given.

In the case of simultaneous use of fibrate preparation and HMG-CoA reductase inhibitor, it is known that rhabdomyolysis will sometimes occur. So, they cannot be used for a patient with renal failure or with impaired renal function. In the above-mentioned combination, there may be some which improve disorder of lipid metabolism without occurrence of rhabdomyolysis.

As other drugs to complement and/or to enhance hypoglycemic effect of the compound represented by the formula (I), or to enhance effect of the treatment of complication of diabetes, for example, sulfonylurea type hypoglycemic agent, biguanide preparation, alfa-glucosidase inhibitor, fast-acting insulin secretion accelerator, insulin preparation, DP (dipeptidyl peptidase) 4 inhibitor, beta-3 adrenaline receptor activator or theraputic agent of complication of diabetes, etc. are given.

As sulfonylurea type hypoglycemic agent, for example, acetohexamide, glibenclamide, gliclazide, glyclopyramide, chlorpropamide, tolazamide, tolbutamide and glimepiride, etc. are given.

As biguanide preparation, for example, Buformin hydrochloride and metformin hydrochloride, etc. are given.

As alfa-glucosidase inhibitor, for example, acarbose and voglibose, etc. are given.

As fast-acting insulin secretion accelerator, for example, nateglinide and repaglinide, etc. are given.

As DP4 inhibitor, for example, NVP-DPP728A, etc. are given.

As beta-3 adrenaline receptor activator, for example, AJ9677, L750355 and CP331648, etc. are given.

As theraputic agent of complication of diabetes, for example, epairestat, etc. are given.

Weight ratio of the compound represented by formula (I) and other drugs is not limited.

Other drugs may be administered as a combination of any two or more drugs.

In other drugs to complement and/or to enhance the preventing and/or treating effect of the compound represented by formula (I), drugs that not only exist now but also may be found in the future on the basis of above mechanisms are included.

When the compound represented by formula (I) which are used in the present invention, or concomitant drug combined the compound represented by formula (I) with other drugs are used for the above-described purpose, it is usually administered systemically or topically via an oral or parenteral route.

The doses to be administered are determined depending upon, for example, age, body weight, symptom, the desired therapeutic effect, the route of administration, and the duration of the treatment. In the human adult, the doses per person are generally from 1 mg to 1000 mg, by oral administration, up to several times per day, and from 1 mg to 100 mg, by parenteral administration (preferably intravenous administration), up to several times per day, or continuous administration from 1 to 24 hours per day from vein.

As mentioned above, the doses to be used depend upon various conditions. Therefore, there are cases in which doses lower than or greater than the ranges specified above may be used.

The compound represented by formula (I) which are used in the present invention, or concomitant drug combined the compound represented by formula (I) with other drugs may be administered in the composition of, for example, solid compositions, liquid compositions or other compositions each for oral administration, or injections, liniments suppositories, eye drops, or inhalations, each for parenteral administration.

Solid compositions for oral administration include compressed tablets, pills, capsules, dispersible powders and granules. Capsules include hard capsules and soft capsules.

In such solid forms, one or more of the active compound (s) may be admixed with vehicles (such as lactose, mannitol, glucose, microcrystalline cellulose, starch), binders (such as hydroxypropyl cellulose, polyvinylpyrrolidone or magnesium metasilicate aluminate), disintegrants (such as cellulose calcium glycolate), lubricants (such as magnesium stearate), stabilizing agents, and solution adjuvants (such as glutamic acid or aspartic acid) and prepared according to methods well known in normal pharmaceutical practice. The solid forms may, if desired, be coated with coating agents (such as sugar, gelatin, hydroxypropyl cellulose or hydroxypropylmethyl cellulose phthalate), or be coated with two or more films. And further, coating may include containment within capsules of absorbable materials such as gelatin.

Liquid forms for oral administration include pharmaceutically acceptable solutions, suspensions and emulsions, syrups and elixirs. In such forms, one or more of the active compound(s) may be dissolved, suspended or emulized into diluent(s) commonly used in the art (such as purified water, ethanol or a mixture thereof). Besides such liquid forms may also comprise some additives, such as wetting agents, suspending agents, emulsifying agents, sweetening agents, flavoring agents, aroma, preservative or buffering agent.

In the parenteral administration, formulation of external use include, for example, ointment, ger, cream, poultice, patch, liniment, atomized agent, inhalation, spray, eye drops and nasal drops, etc. They includes one or more of the active compound(s) and be prepared by known method or usual method.

Ointment is prepared by known method or usual method. For example, it is prepared by levigation or fusion of one or more of the active compound(s) and substrate. The substrate of ointment is selected from known or usual one. For example, higher fatty acid or higher fatty acid ester (adipic acid, myristic acid, palmitic acid, stearic acid, oleic acid, adipic acid ester, myristic acid ester, palmitic acid ester, stearic acid ester, oleic acid ester, etc.), wax (yellow beeswax, Spermaceti, ceresin, etc.), surfactant (polyoxyethylene alkyl ether phosphoric acid ester, etc.), higher alcohol (cetanol, stearil alcohol, cetostearyl alcohol, etc.), silicon oil (dimethyl polysiloxane, etc.), hydrocarbon (hydrophilic petrolatum, white petrolatum, purified lanolin, light liquid paraffin, etc.), glycol (ethylene glycol, diethylene glycol, propylene glycol, polyethylene glycol, macrogol, etc.), vegetable oil (castor oil, olive oil, sesame oil, turpentine oil, etc.), animal oil (mink oil, egg yolk oil, squalane, squalene, etc.), water, absorption accelerator, skin fit inhibitor, etc. are used as single substance selected from them or mixture which consists of two or more kinds that is selected from them. Moreover, humectant, preservative agent, stabilizer, antioxidative agent, fragrant materials, etc. may be contained.

Ger is prepared by known method or usual method. For example, it is prepared by fusion of one or more of the active compound(s) and substrate. The substrate of gel is selected from known or usual one. For example, lower alcohol (ethanol, isopropylalcohol, etc.), gelling agent (carboxy methyl cellulose, hydroxy ethyl cellulose, hydroxy propyl cellulose, ethyl cellulose, etc.), neutralizing agent, (triethanolamine, diisopropanolamine, etc.), surfactant, (polyethylene glycol monostearate, etc.), gum, water, absorption accelerator, skin fit inhibitor, etc. are used as single substance selected from them or mixture which consists of two or more kinds that is selected from them. Moreover, preservative agent, antioxidative agent, fragrant materials, etc. may be contained.

Cream is prepared by known method or usual method. For example, it is prepared by fusion or emulsification of one or more of the active compound(s) and substrate. The substrate of cream is selected from known or usual one. For example, higher fatty acid ester, lower alcohol, hydrocarbon, polyalcohol (propylene glycol, 1,3-butylene glycol, etc.) higher alcohol (2-hexyldecanol, cetanol, etc.), emulsifying agent (polyoxyethylene anlyl ether, fatty acid ester, etc.), water, absorption accelerator, skin fit inhibitor, etc. are used as single substance selected from them or mixture which consists of two or more kinds that is selected from them. Moreover, preservative agent, antioxidative agent, fragrant materials, etc. may be contained.

Poultice is prepared by known method or usual method. For example, it is prepared by fusion of one or more of the active compound(s) and substrate, and then the kneaded one is laid over support medium. The substrate for poultice is selected from known or usual one. For example, thickening agent (polyacrylic acid, polyvinylpyrolidone, gum acacia, starch, gelatin, methyl cellulose, etc.), bulking agent (kaolin, zinc oxide, talc, calcium, magnesium, etc.), water, solubilizing agent, thickener, skin fit inhibitor, etc. are used as single substance selected from them or mixture which consists of two or more kinds that is selected from them. Moreover, preservative agent, antioxidative agent, fragrant materials, etc. may be contained.

Patch is prepared by known method or usual method. For example, it is prepared by fusion of one or more of the active compound(s) and substrate, and then laid over support medium. The substrate for patch is selected from known or usual one. For example, polymer substrate, fat, higher fatty acid, thickener, skin fit inhibitor, etc. are used as single substance selected from them or mixture which consists of two or more kinds that is selected from them. Moreover, preservative agent, antioxidative agent, fragrant materials, etc. may be contained.

Liniment is prepared by known method or usual method. For example, one or more of the active compound(s) may be dissolved, suspended or emulsified in water, alcohol (ethanol, polyethylene glycol, etc.), higher fatty acid, glycerin, soap, emulsifying agent, suspending agent, etc. as single substance selected from them or mixture which consists of two or more kinds that is selected from them. Moreover, preservative agent, antioxidative agent, fragrant materials, etc. may be contained.

Atomized agent, inhalation and spray may comprise in addition to a diluent, a stabilizer such as sodium bisulfite and an isotonization buffer such as sodium chloride, sodium citrate or citric acid. The preparation process of sprays is described in detail in, for example, U.S. Pat. Nos. 2,868,691 and 3,095,355. Moreover, it may be aerosol.

Injections for parenteral administration include sterile aqueous, suspensions, emulsions and solid forms which are dissolved or suspended into solvent(s) for injection immediately before use. In injections, one or more of the active compound(s) may be dissolved, suspended or emulized into solvent(s). The solvents may include distilled water for injection, physiological salt solution, vegetable oil, propylene glycol, polyethylene glycol, alcohol, e.g. ethanol or a mixture thereof.

Injections may comprise some additives, such as stabilizing agents, solution adjuvants (such as glutamic acid, aspartic acid or POLYSORBATE80 (registered trade mark)), suspending agents, emulsifying agents, soothing agent, buffering agents, preservative. They may be sterilized at a final step, or may be prepared and compensated according to sterile methods. They may also be manufactured in the form of sterile solid forms, for example, freeze-dried products, which may be dissolved in sterile water or some other sterile diluent(s) for injection immediately before use.

The dosage of inhalations for parenreral administration include aerosol, powders for inhalation or liquids for inhalation. The liquids for inhalation may be dissolved or suspended in water or the other appropriate solvent as needed.

Such inhalations are prepared in a known method. For example, a liquid for inhalation is prepared by selecting proper additives from an antiseptic (such as benzalkonium chloride or p-aminobenzonic acid), a coloring agent, a buffering agent (such as sodium phosphate or sodium acetate), an isotonizing agent (such as sodium chloride or concentrated glycerin), thickening agent (such as carboxyvinylpolymer), or an accelerator of absorption, etc., if necessary.

A powder for inhalation is prepared by selecting proper additives from a lubricant agent (such as stearin acid and the salt thereof), a binding agent, (such as starch, dextrin), a diluting agent (such as lactose, cellulose), a coloring agent, an antiseptic (such as benzalkonium chloride or p-aminobenzonic acid), an accelerator of absorption, etc., if necessary.

In case of administration of liquid for inhalation, spray (atomizer, nebulizer) is usually used and in case of administration of powder for inhalation, inhalation administration apparatus for powder agents is usually used.

The other compositions for parenteral administration include suppositories for intrarectal administration and pessaries for vaginal administration which comprise one or more of the active substance(s) and may be prepared by methods known per se.

BEST MODE FOR CARRYING OUT THE INVENTION

The present invention is explained below in detail based on Reference Examples and Examples, however, the present invention is not limited thereto.

The solvents in the parentheses show the developing or eluting solvents and the ratios of the solvents used are by volume in chromatographic separations or TLC. The solvents in the parentheses in NMR show the solvents for measurement.

REFERENCE EXAMPLE 1

5-Methoxymethoxyquinoline

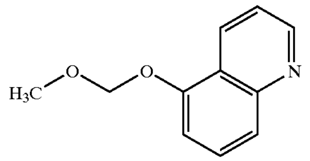

A solution of 5-hydroxyquinoline (10.3 g) in dimethylformamide (140 ml) was ice-cooled. To the solution was added sodium hydride (3.0 g, 62.6% in oil) and the mixture was stirred at 0° C. for 15 minutes. To the reaction mixture was added methoxymethyl chloride (6.5 ml) and then the mixture was stirred at 0° C. for 2 hours. To the reaction mixture was added ice. The reaction mixture was stirred and then diluted with water. The aqueous layer was extracted with ethyl acetate. The combined organic layer was washed with 1N aqueous solution of sodium hydroxide, water and a saturated aqueous solution of sodium chloride subsequently, dried over anhydrous magnesium sulfate, and then concentrated to give the title compound (10.4 g) having the following physical data. The obtained compound was used without purification in the subsequent reaction.

TLC: Rf 0.33 (hexane:ethyl acetate=2:1);

NMR ($CDCl_3$): δ 8.91 (dd, J=4.5, 1.5 Hz, 1H), 8.59 (ddd, J=7.5, 0.9, 0.9 Hz, 1H), 7.76 (dd, J=8.4, 0.9 Hz, 1H), 7.60 (dd, J=8.4, 8.4 Hz, 1H), 7.39 (dd, J=8.4, 4.5 Hz, 1H), 7.15 (d, J=7.5 Hz, 1H), 5.39 (s, 2H), 3.54 (s, 3H).

REFERENCE EXAMPLE 2

5-Methoxymethoxy-1,2,3,4-tetrahydroquinoline

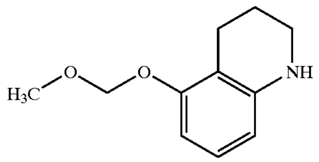

To a solution of the compound prepared in reference example 1 (10.4 g) in methanol (100 ml) was added platinum dioxide (1.0 g) under an atmosphere of argon. The atmosphere was substituted with hydrogen. The reaction mixture was stirred at room temperature for 24 hours. The reaction mixture was filtered using cellite. The filtrate was concentrated. The residue was purified by column chromatography on silica gel (hexane:ethyl acetate=4:1) to give the title compound (8.7 g) having the following physical data.

TLC: Rf 0.67 (hexane:ethyl acetate=4:1);

NMR ($CDCl_3$): δ 6.89 (dd, J=8.1, 8.1 Hz, 1H), 6.3.8 (dd, J=8.1, 0.9 Hz, 1H), 6.18 (d, J=8.1 Hz, 1H), 5.17 (s, 2H), 3.47 (s, 3H), 3.25 (t, J=5.4 Hz, 2H), 2.69 (t, J=6.6 Hz, 2H), 1.92 (m, 2H).

REFERENCE EXAMPLE 3

3-(5-Methoxymethoxy-1,2,3,4-tetrahydroquinolin-1-yl)-3-oxopropanoic acid ethyl ester

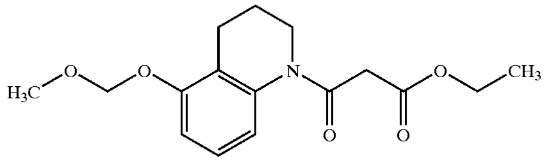

A solution of the compound (4.1 g) prepared in reference example 2 in methlene chloride (80 ml) was ice-cooled. To the mixture was added triethylamine (4.4 ml) and ethyl malonyl chloride (3.2 ml), and then the mixture was stirred at 0° C. for 30 minutes. The organic layer was washed with a saturated aqueous sodium hydrogen carbonate solution, dried over anhydrous magnesium sulfate and concentrated. The residue was purified by column chromatography on silica gel (hexane:ethyl acetate=2:1) to give the title compound (6.3 g) having the following physical data.

TLC: Rf 0.19 (hexane:ethyl acetate=3:1);

NMR ($CDCl_3$): δ 7.12 (dd, J=8.4, 8.4 Hz, 1H), 7.05–6.75 (br, 1H), 6.93 (d, J=8.4 Hz, 1H), 5.21 (s, 2H), 4.16 (q, J=7.2 Hz, 2H), 3.83 (br, 2H), 3.62 (s, 2H), 3.48 (s, 3H), 2.74 (t, J=6.9 Hz, 2H), 1.98 (m, 2H), 1.24 (t, J=7.2 Hz, 3H).

REFERENCE EXAMPLE 4

3-(5-Methoxymethoxy-1,2,3,4-tetrahydroquinolin-1-yl)propanoic acid ethyl ester

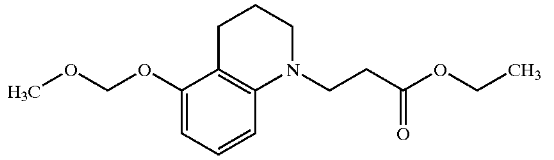

To the solution of the compound (5.1 g) prepared in reference example 3 in anhydrous tetraydrofuran (150 ml) was added borane-dimethylsulfide complex (24 ml, 2M solution of tetrahydrofuran) under argon atmosphere. The reaction mixture was stirred at 4° C. overnight and then stirred at room temperature for 3 hours. To the reaction mixture was added acetone. The mixture was stirred and then concentrated. The residue was diluted with ethyl acetate, washed with 1N hydrochloric acid, water and a saturated aqueous solution of sodium chloride subsequently, dried over anhydrous magnesium sulfate and then concentrated. The residue was purified by column chromatography on silica gel (hexane:ethyl acetate=4:1) to give the title compound (1.2 g) having the following physical data.

TLC: Rf 0.71 (hexane:ethyl acetate=2:1);

NMR ($CDCl_3$): δ 6.99 (dd, J=8.1, 8.1 Hz, 1H), 6.41 (d, J=8.1 Hz, 1H), 6.34 (d, J=8.1 Hz, 1H), 5.16 (s, 2H), 4.14 (q, J=7.2 Hz, 2H), 3.60 (t, J=7.2 Hz, 2H), 3.47 (s, 3H), 3.24 (t, J=5.4 Hz, 2H), 2.69 (t, J=6.6 Hz, 2H), 2.57 (t, J=7.2 Hz, 2H), 1.91 (m, 2H), 1.25 (t, J=7.2 Hz, 3H).

REFERENCE EXAMPLE 5

3-(5-Hydroxy-1,2,3,4-tetrahydroquinolin-1-yl)propanoic acid ethyl ester

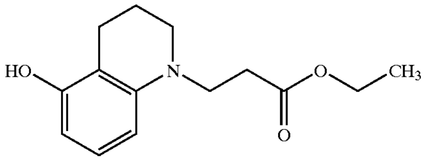

To a solution of the compound (1.2 g) prepared in reference example 4 in ethanol (25 ml) was added 4N hydrochloric acid in dioxane (4 ml). The mixture was stirred at room temperature for 24 hours. The reaction mixture was poured into a saturated aqueous sodium hydrogen carbonate solution, and then the aqueous layer was extracted with ethyl acetate. The organic layer was washed with a saturated aqueous solution of sodium chloride, dried over anhydrous magnesium sulfate and concentrated to give the title compound (1.1 g) having the following physical data.

TLC: Rf 0.32 (hexane:ethyl acetate=4:1);

NMR ($CDCl_3$): δ 6.92 (dd, J=8.1, 8.1 Hz, 1H), 6.25 (d, J=8.1 Hz, 1H), 6.14 (m, 1H), 4.61 (brs, 1H), 4.14 (q, J=7.2 Hz, 2H), 3.60 (dd, J=7.5, 7.5 Hz, 2H), 3.25 (m, 2H), 2.65 (t, J=6.6 Hz, 2H), 2.58 (m, 2H), 1.95 (m, 2H), 1.26 (t, J=7.2 Hz, 3H).

EXAMPLE 1

3-(5-(2-(2-(4-Methylphenyl)-5-methyloxazol-4-yl)ethoxy)-1,2,3,4-tetrahydroquinolin-1-yl)propanoic acid ethyl ester

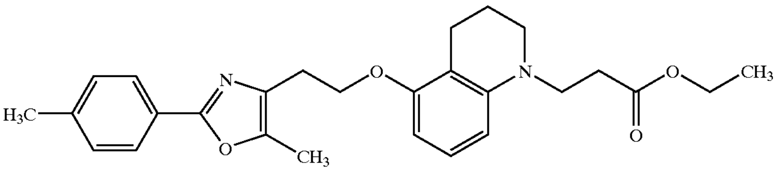

To a solution of the compound prepared in reference example 5 (500 mg) and 2-(5-methyl-2-(4-methylphenyl)oxazol-4-yl)ethanol (871 mg; it was prepared according to the procedure described in J. Med. Chem, 35, 1853–1864 (1992).) in methylene chloride (20 ml) was added triphenylphosphine (1.0 g) and 1,1'-(azodicarbonyl)dipiperidine (1.0 g). The mixture was stirred at room temperature for 2 days. The reaction mixture was concentrated. To the residue was added diethyl ether, and then insoluble material was filtered off. The filtrate was washed with 2N aqueous solution of sodium hydroxide, water and a saturated aqueous solution of sodium chloride subsequently, dried over anhydrous magnesium sulfate and then concentrated. The residue was purified by column chromatography on silica gel (hexane:ethyl acetate=5:1) to give the compound of the present invention (721 mg) having the following physical data.

TLC: Rf 0.58 (hexane:ethyl acetate=2:1);

NMR ($CDCl_3$): δ 7.86 (d, J=7.8 Hz, 2H), 7.23 (d, J=7.8 Hz, 2H), 6.98 (dd, J=8.4, 8.4 Hz, 1H), 6.29 (d, J=8.4 Hz, 1H), 6.25 (d, J=8.4 Hz, 1H), 4.19 (t, J=6.6 Hz, 2H), 4.12 (q, J=6.9 Hz, 2H), 3.59 (t, J=7.2 Hz, 2H), 3.21 (t, J=5.4 Hz, 2H), 2.95 (t, J=6.6 Hz, 2H), 2.61 (t, J=6.9 Hz, 2H), 2.58 (t, J=7.2 Hz, 2H), 2.38(s, 3H), 2.35 (s, 3H), 1.88 (m, 2H), 1.24 (t, J=6.9 Hz, 3H).

EXAMPLE 1(1) TO EXAMPLE 1(11)

The following compounds of the present invention were obtained in the same manner as in Example 1 using a corresponding derivative instead of 2-(5-methyl-2-(4-methylphenyl)oxazol-4-yl)ethanol.

EXAMPLE 1(1)

3-(5-(2-(2-(Piperidin-1-yl)-5-methylthiazol-4-yl) ethoxy)-1,2,3,4-tetrahydroquinolin-1-yl)propanoic acid ethyl ester

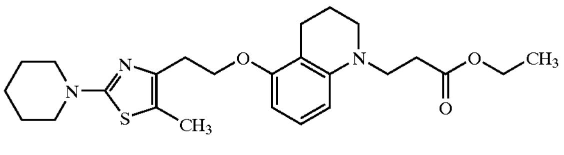

TLC: Rf 0.70 (hexane:ethyl acetate=2:1);

NMR ($CDCl_3$): δ 6.97 (dd, J=8.1, 8.1 Hz, 1H), 6.28 (d, J=8.1 Hz, 1H), 6.25 (d, J=8.1 Hz, 1H), 4.17–4.09 (m, 2H), 3.59 (t, J=7.8 Hz, 2H), 3.35(m, 4H), 3.20 (t, J=8.4 Hz, 2H), 2.92 (t, J=6.9 Hz, 2H), 2.61 (t, J=6.3 Hz, 2H), 2.58 (t, J=6.9 Hz, 2H), 2.23(s, 3H), 1.88 (m, 2H), 1.62 (m, 6H), 1.25 (t, J=6.9 Hz, 3H).

EXAMPLE 1(2)

3-(5-(2-(2-(4-Trifluoromethylphenyl)-5-methyloxazol-4-yl)ethoxy)-1,2,3,4-tetrahydroquinolin-1-yl)propanoic acid ethyl ester

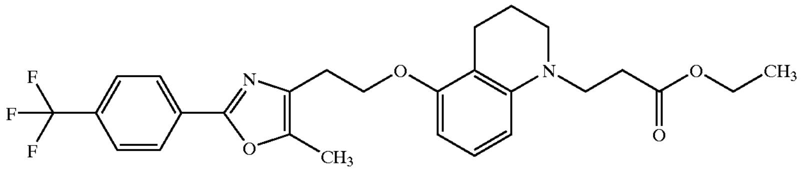

TLC: Rf 0.73 (hexane:ethyl acetate=1:1);

NMR ($CDCl_3$): δ 8.08 (d, J=8.4 Hz, 2H), 7.68 (d, J=8.4 Hz, 2H), 6.99 (d, J=8.4 Hz, 1H), 6.29 (d, J=8.4 Hz, 1H), 6.25 (d, J=8.4 Hz, 1H), 4.21 (t, J=6.3 Hz, 2H), 4.12 (q, J=7.2 Hz, 2H), 3.59 (t, J=7.2 Hz, 2H), 3.21 (t, J=5.7 Hz, 2H), 2.96 (t, J=6.3 Hz, 2H), 2.61 (t, J=6.6 Hz, 2H), 2.55 (t, J=7.2 Hz, 2H), 2.39 (s, 3H), 1.92–1.84 (m, 2H), 1.25 (t, J=7.2 Hz, 3H).

EXAMPLE 1(3)

3-(5-(2-(2-(4-Ethylphenyl)-5-methyloxazol-4-yl) ethoxy)-1,2,3,4-tetrahydroquinolin-1-yl)propanoic acid ethyl ester

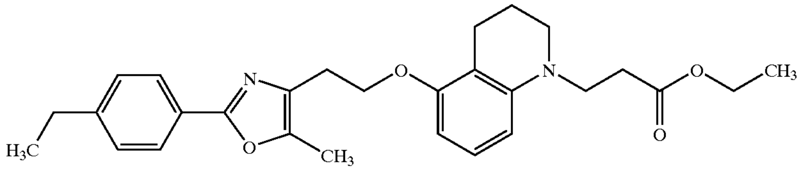

TLC: Rf 0.65 (hexane:ethyl acetate=2:1);

NMR ($CDCl_3$): δ 7.88 (d, J=7.8 Hz, 2H), 7.25 (d, J=7.8 Hz, 2H), 6.98 (dd, J=8.7, 8.1 Hz, 1H), 6.28 (d, J=8.1 Hz, 1H), 6.25 (d, J=8.7 Hz, 1H), 4.20 (t, J=6.6 Hz, 2H), 4.12 (q, J=8.4 Hz, 2H), 3.59 (t, J=6.9 Hz, 2H), 3.21 (t, J=5.4 Hz, 2H), 2.95 (t, J=6.0 Hz, 2H), 2.68 (q, J=7.5 Hz, 2H), 2.61 (t, J=6.6 Hz, 2H), 2.55 (t, J=6.9 Hz, 2H), 2.35 (s, 3H), 1.92–1.87 (m, 2H), 1.25 (t, J=7.5 Hz, 3H), 1.24 (t, J=8.4 Hz, 3H).

EXAMPLE 1(4)

3-(5-(2-(2-(1,3-Dioxaindan-5-yl)-5-methyloxazol-4-yl)ethoxy)-1,2,3,4-tetrahydroquinolin-1-yl)propanoic acid ethyl ester

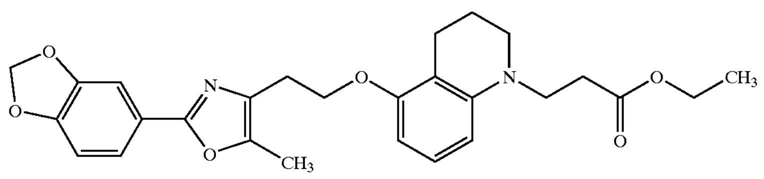

TLC: Rf 0.61 (hexane:ethyl acetate=2:1);

NMR ($CDCl_3$): δ 7.51 (dd, J=8.1, 1.8 Hz, 1H), 7.43 (d, J=1.8 Hz, 1H), 6.98 (dd, J=8.4, 8.1 Hz, 1H), 6.85 (d, J=8.1 Hz, 1H), 6.29 (d, J=8.1 Hz, 1H), 6.25 (d, J=8.4 Hz, 1H), 6.01 (s, 2H), 4.19 (t, J=6.3 Hz, 2H), 4.12 (q, J=7.2 Hz, 2H), 3.59 (t, J=7.2 Hz, 2), 3.21 (t, J=5.7 Hz, 2H), 2.93 (t, J=6.3 Hz, 2H), 2.61 (t, J=6.6 Hz, 2H), 2.56 (t, J=7.2 Hz, 2H), 2.34 (s, 3H), 1.93–1.85 (m, 2H), 1.25 (t, J=7.2 Hz, 3H).

EXAMPLE 1(5)

3-(5-(2-(2-(4-Chlorophenyl)-5-methyloxazol-4-yl)ethoxy)-1,2,3,4-tetrahydroquinolin-1-yl)propanoic acid ethyl ester

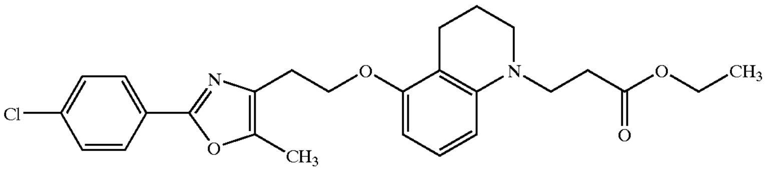

TLC: Rf 0.55 (hexane:ethyl acetate=2:1);

NMR ($CDCl_3$): δ 7.90 (d, J=8.4 Hz, 2H), 7.39 (d, J=8.4 Hz, 2H), 6.98 (dd, J=8.1, 8.1 Hz, 1H), 6.29 (d, J=8.1 Hz, 1H), 6.24 (d, J=8.1 Hz, 1H), 4.20 (t, J=6.3 Hz, 2H), 4.12 (q, J=7.2 Hz, 2H), 3.59 (t, J=6.9 Hz, 2H), 3.21 (t, J=5.4 Hz, 2H), 2.95 (t, J=6.3 Hz, 2H), 2.61 (t, J=6.9 Hz, 2H), 2.55 (t, J=7.2 Hz, 2H), 2.36 (s, 3H), 1.88 (m, 2H), 1.25 (t, J=7.2 Hz, 3H).

EXAMPLE 1(6)

3-(5-(2-(2-Phenyl-5-methyloxazol-4-yl)ethoxy)-1,2,3,4-tetrahydroquinolin-1-yl)propanoic acid ethyl ester

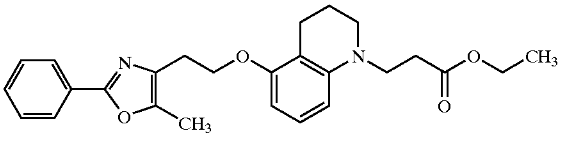

TLC: Rf 0.35 (hexane:ethyl acetate=4:1);

NMR ($CDCl_3$): δ 7.99–7.96 (m, 2H), 7.42–7.40 (m, 3H), 6.99 (t, J=8.1 Hz, 1H), 6.29 (d, J=8.1 Hz, 1H), 6.25 (d, J=8.1 Hz, 1H), 4.21 (t, J=6.6 Hz, 2H), 4.12 (q, J=7.2 Hz, 2H), 3.59 (t, J=7.2 Hz, 2H), 3.21 (t, J=5.7 Hz, 2H), 2.96 (t, J=6.6 Hz, 2H), 2.62 (t, J=6.6 Hz, 2H), 2.56 (t, J=7.2 Hz, 2H), 2.36 (s, 3H), 1.89 (m, 2H), 1.26 (t, J=7.2 Hz, 3H).

EXAMPLE 1(7)

3-(5-(2-(2-(4-Trifluoromethoxyphenyl)-5-methyloxazol-4-yl)ethoxy)-1,2,3,4-tetrahydroquinolin-1-yl)propanoic acid ethyl ester

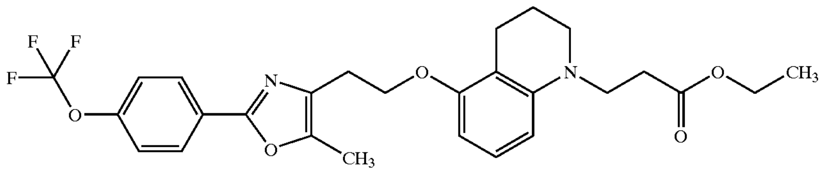

TLC: Rf 0.43 (hexane:ethyl acetate=4:1);

NMR ($CDCl_3$): δ 7.99 (m 2H), 7.26 (m 2H), 6.99 (t, J=8.4 Hz, 1H), 6.29 (d, J=8.4 Hz, 1H), 6.25 (d, J=8.4 Hz, 1H), 4.20

(t, J=6.6 Hz, 2H), 4.12 (q, J=7.2 Hz, 2H), 3.59 (t, J=7.2 Hz, 2H), 3.21 (t, J=5.7 Hz, 2H), 2.95 (t, J=6.6 Hz, 2H), 2.61 (t, J=6.6 Hz, 2H), 2.56 (t, J=7.2 Hz, 2H), 2.37 (s, 3H), 1.88 (m, 2H), 1.25 (t, J=7.2 Hz, 3H).

EXAMPLE 1(8)

3-(5-(2-(2-(4-Methoxyphenyl)-5-methyloxazol-4-yl)ethoxy)-1,2,3,4-tetrahydroquinolin-1-yl)propanoic acid ethyl ester

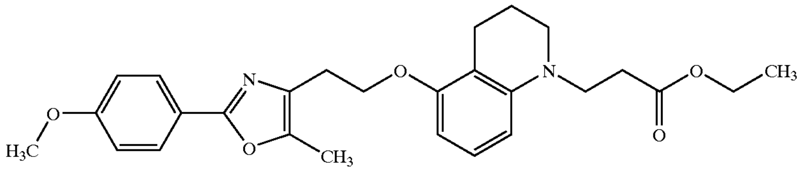

TLC: Rf 0.36 (hexane:ethyl acetate=4:1);

NMR ($CDCl_3$): δ 7.90 (d, J=8.7 Hz, 2H), 7.01 (t, J=8.1 Hz, 1H), 6.94 (d, J=8.7 Hz, 2H), 6.29 (d, J=8.1 Hz, 1H), 6.25 (d, J=8.1 Hz, 1H), 4.20 (t, J=6.6 Hz, 2H), 4.12 (q, J=7.2 Hz, 2H), 3.85 (s, 3H), 3.59 (t, J=7.2 Hz, 2H), 3.21 (t, J=5.4 Hz, 2H), 3.11 (t, J=6.6 Hz, 2H), 2.62 (t, J=6.6 Hz, 2H), 2.56 (t, J=7.2 Hz, 2H), 2.36 (s, 3H), 1.89 (m, 2H), 1.25 (t, J=7.2 Hz, 3H).

EXAMPLE 1(9)

3-(5-(2-(2-(4-t-Butylphenyl)-5-methyloxazol-4-yl)ethoxy)-1,2,3,4-tetrahydroquinolin-1-yl)propanoic acid ethyl ester

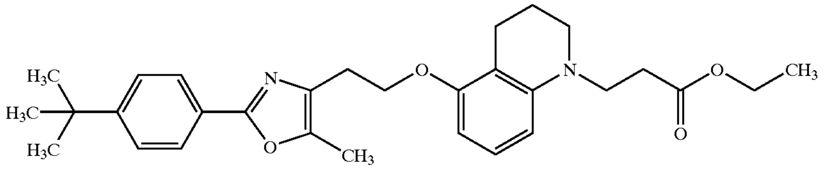

TLC: Rf 0.66 (hexane:ethyl acetate=4:1);

NMR ($CDCl_3$): δ 7.89 (d, J=8.7 Hz, 2H), 7.43 (d, J=8.7 Hz, 2H), 6.98 (dd, J=8.4, 8.1 Hz, 1H), 6.29 (d, J=8.4 Hz, 1H), 6.25 (d, J=8.1 Hz, 1H), 4.20 (t, J=6.6 Hz, 2H), 4.12 (q, J=7.2 Hz, 2H), 3.59 (t, J=7.2 Hz, 2H), 3.21 (t, J=5.4 Hz, 2H), 2.95 (t, J=6.6 Hz, 2H), 2.61 (t, J=6.6 Hz, 2H), 2.56 (t, J=7.2 Hz, 2H), 2.35 (s, 3H), 1.89 (m, 2H), 1.34 (s, 9H), 1.25 (t, J=7.2 Hz, 3H).

EXAMPLE 1(10)

3-(5-(2-(2-(4-Fluorophenyl)-5-methyloxazol-4-yl)ethoxy)-1,2,3,4-tetrahydroquinolin-1-yl)propanoic acid ethyl ester

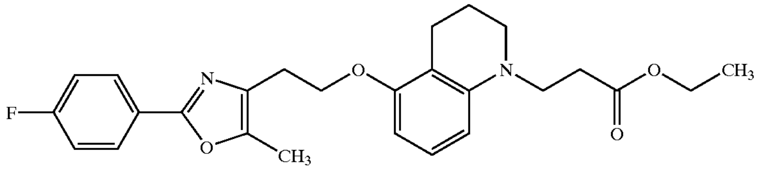

TLC: Rf 0.41 (hexane:ethyl acetate=4:1);

NMR ($CDCl_3$): δ 7.97 (d, J=8.7 Hz, 1H), 7.95 (d, J=8.7 Hz, 1H), 7.11 (d, J=8.7 Hz, 2H), 6.98 (dd, J=8.4 Hz, 1H), 6.29 (d, J=8.4 Hz, 1H), 6.25 (d, J=8.4 Hz, 1H), 4.20 (t, J=6.6 Hz, 2H), 4.12 (q, J=7.2 Hz, 2H), 3.59 (t, J=7.2 Hz, 2H), 3.21 (t, J=5.4 Hz, 2H), 2.94 (t, J=6.6 Hz, 2H), 2.91 (t, J=6.6 Hz, 2H), 2.55 (t, J=7.2 Hz, 2H), 2.35 (s, 3H), 1.88 (m, 2H), 1.25 (t, J=7.2 Hz, 3H).

EXAMPLE 1(11)

3-(5-(2-(2-(4-Propylphenyl)-5-methyloxazol-4-yl)ethoxy)-1,2,3,4-tetrahydroquinolin-1-yl)propanoic acid ethyl ester TLC: Rf 0.40 (hexane:ethyl acetate=4:1);

NMR ($CDCl_3$): δ 7.87 (d, J=8.4 Hz, 2H), 7.23 (d, J=8.4 Hz, 2H), 6.98 (dd, J=8.1, 8.1 Hz, 1H), 6.29 (m, 2H), 4.19 (t, J=6.6 Hz, 2H), 4.12 (q, J=8.4 Hz, 2H), 3.57 (t, J=6.6 Hz, 2H), 3.19 (m, 2H), 2.95 (t, J=6.6 Hz, 2H), 2.61 (m, 6H), 2.34 (s, 3H), 1.88 (m, 2H), 1.66 (m, 2H), 1.24 (t, J=8.4 Hz, 3H), 0.93 (t, J=7.2 Hz, 3H).

EXAMPLE 2

3-(5-(2-(2-(4-Methylphenyl)-5-methyloxazol-4-yl)ethoxy)-1,2,3,4-tetrahydroquinolin-1-ylpropanoic acid

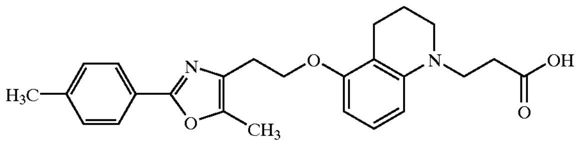

The compound prepared in example 1 (718 mg) was dissolved in a mixture of ethanol (25 mL) and tetrahydrofuran (25 ml). To the solution was added 2N aqueous solution of sodium hydroxide (2.4 ml) and the mixture was stirred at room temperature overnight. The reaction mixture was ice-cooled. To the reaction mixture was added 2N hydrochloric acid in order to neutralize. The mixture was concentrated. The residue was washed with water and then filtrated. The obtained solid was dried at 50° C. under reduced pressure and then recrystallized from methanol to give the compound of the present invention having the following physical data.

TLC: Rf 0.41 (chloroform:methanol=10:1);

NMR ($CDCl_3$): δ 7.86 (d, J=8.1 Hz, 2H), 7.22 (d, J=8.1 Hz, 2H), 6.99 (dd, J=8.4, 8.4 Hz, 1H), 6.30 (m, 2H), 4.19 (t, J=6.6 Hz, 2H), 3.59 (t, J=7.2 Hz, 2H), 3.20 (t, J=5.4 Hz, 2H), 2.95 (t, J=6.6 Hz, 2H), 2.62 (m, 4H), 2.38 (s, 3H), 2.35 (s, 3H), 1.89 (m, 2H).

EXAMPLE 2(1) TO EXAMPLE 2(11)

The following compounds of the present invention were obtained in the same manner as in Example 1 using a corresponding compounds prepared in example 1(1) to 1(11) instead of the compound prepared in Example 1.

EXAMPLE 2(1)

3-(5-(2-(2-(Piperidin-1-yl)-5-methylthiazol-4-yl)ethoxy)-1,2,3,4-tetrahydroquinolin-1-yl)propanoic acid

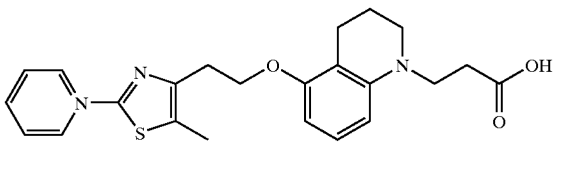

TLC: Rf 0.35 (chloroform:methanol=10:1);

NMR ($CDCl_3$): δ 6.99 (dd, J=8.4, 8.4 Hz, 1H), 6.30 (m, 2H), 4.15 (t, J=6.9 Hz, 2H), 3.58 (t, J=7.2 Hz, 2H), 3.35 (m, 4H), 3.20 (t, J=5.4 Hz, 2H), 2.92 (t, J=6.9 Hz, 2H), 2.61 (m, 4H), 2.23 (s, 3H), 1.89 (m, 2H), 1.62 (m, 6H).

EXAMPLE 2(2)

3-(5-(2-(2-(4-Trifluoromethylphenyl)-5-methyloxazol-4-yl)ethoxy)-1,2,3,4-tetrahydroquinolin-1-yl)propanoic acid

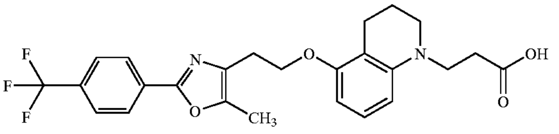

TLC: Rf 0.62 (hexane:ethyl acetate=1:4);

NMR ($CDCl_3$): δ 8.08 (d, J=8.1 Hz, 2H), 7.68 (d, J=8.1 Hz, 2H), 7.00 (t, J=8.4 Hz, 1H), 6.32 (d, J=8.4 Hz, 1H), 6.28 (d, J=8.4 Hz, 1H), 4.21 (t, J=6.6 Hz, 2H), 3.60 (t, J=6.9 Hz, 2H), 3.21 (t, J=5.7 Hz, 2H), 2.98 (t, J=6.6 Hz, 2H), 2.62 (m, 4H), 2.39 (s, 3H), 1.90 (m, 2H).

EXAMPLE 2(3)

3-(5-(2-(2-(4-Ethylphenyl)-5-methyloxazol-4-yl)ethoxy)-1,2,3,4-tetrahydroquinolin-1-yl)propanoic acid

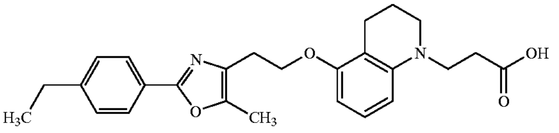

TLC: Rf 0.33 (hexane:ethyl acetate=1:5);

NMR ($CDCl_3$): δ 7.88 (d, J=8.1 Hz, 2H), 7.25 (d, J=8.1 Hz, 2H), 7.00 (dd, J=8.4, 8.1 Hz, 1H), 6.31 (m, 2H), 4.20 (t, J=6.6 Hz, 2H), 3.59 (J=6.9 Hz, 2H), 3.49 (m, 2H), 3.21 (t, J=5.4 Hz, 2H), 2.96 (t, J=6.9 Hz, 2H), 2.68 (q, J=7.5 Hz, 2H), 2.62 (t, J=6.6 Hz, 2H), 2.36 (s, 3H), 1.90 (m, 2H), 1.26 (t, J=7.5 Hz, 3H).

EXAMPLE 2(4)

3-(5-(2-(2-(1,3-Dioxaindan-5-yl)-5-methyloxazol-4-yl)ethoxy)-1,2,3,4-tetrahydroquinolin-1-yl)propanoic acid

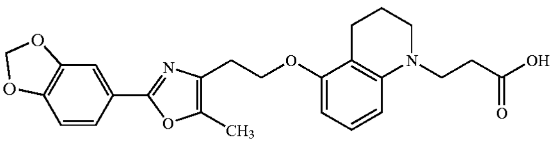

TLC: Rf 0.46 (hexane:ethyl acetate=1:5);

NMR ($CDCl_3$): δ 7.51 (dd, J=8.1, 1.8 Hz, 1H), 7.43 (d, 1.8 Hz, 1H), 6.99 (t, J=8.4 Hz, 1H), 6.84 (d, J=8.1 Hz, 1H), 6.29 (t, J=8.4 Hz, 2H), 6.01 (s, 2H), 4.19 (t, J=6.6 Hz, 2H), 3.59 (t, J=7.2 Hz, 2H), 3.21 (t, J=5.4 Hz, 2H), 2.94 (t, J=6.6 Hz, 2H), 2.62 (m, 4H), 2.34 (s, 3H), 1.89 (m, 2H).

EXAMPLE 2(5)

3-(5-(2-(2-(4-Chlorophenyl)-5-methyloxazol-4-yl)ethoxy)-1,2,3,4-tetrahydroquinolin-1-yl)propanoic acid

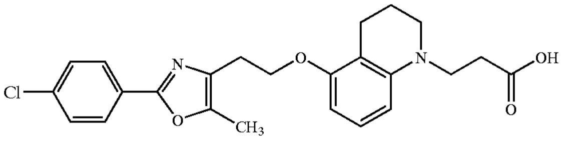

TLC: Rf 0.30 (hexane:ethyl acetate=1:5);

NMR ($CDCl_3$): δ 7.90 (d, J=8.7 Hz, 2H), 7.40 (d, J=8.7 Hz, 2H), 7.00 (dd, J=8.4, 8.4 Hz, 1H), 6.33 (d, J=8.4 Hz, 1H), 6.29 (d, J=8.4 Hz, 1H), 4.20 (t, J=6.6 Hz, 2H), 3.59 (t, J=7.2 Hz, 2H), 3.21 (m, 2H), 2.96 (t, J=6.6 Hz, 2H), 2.62 (t, J=7.2 Hz, 2H), 2.61 (m, 2H), 2.36 (s, 3H), 1.90 (m, 2H).

EXAMPLE 2(6)

3-(5-(2-(2-Phenyl-5-methyloxazol-4-yl)ethoxy)-1,2,3,4-tetrahydroquinolin-1-yl)propanoic acid

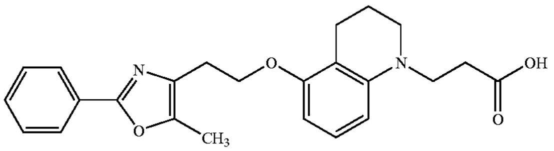

TLC: Rf 0.57 (hexane:ethyl acetate=1:4);

NMR ($CDCl_3$): δ 7.96 (m, 2H), 7.41 (m, 3H), 7.00 (dd, J=8.4, 8.1 Hz, 1H), 6.33 (d, J=8.4 Hz, 1H), 6.30 (d, J=8.1 Hz, 1H), 4.21 (t, J=6.6 Hz, 2H), 3.59 (t, J=6.9 Hz, 2H), 3.21 (t, J=5.7 Hz, 2H), 2.97 (t, J=6.6 Hz, 2H), 2.63 (t, J=6.9 Hz, 4H), 2.37 (s, 3H), 1.90 (m, 2H).

EXAMPLE 2(7)

3-(5-(2-(2-(4-Trifluoromethoxyphenyl)-5-methyloxazol-4-yl)ethoxy)-1,2,3,4-tetrahydroquinolin-1-yl)propanoic acid

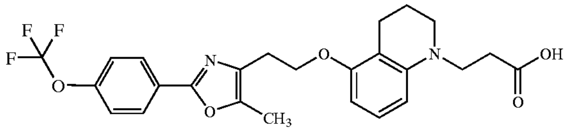

TLC: Rf 0.64 (hexane:ethyl acetate=1:4);

NMR ($CDCl_3$): δ 8.00 (d, J=8.7 Hz, 2H), 7.26 (d, J=8.7 Hz, 2H), 7.00 (t, J=8.1 Hz, 1H), 6.32 (d, J=8.1 Hz, 1H), 6.29 (d, J=8.1 Hz, 1H), 4.20 (t, J=6.3 Hz, 2H), 3.59 (dd, J=7.5, 6.9 Hz, 2H), 3.21 (t, J=5.4 Hz, 2H), 2.96 (t, J=6.3 Hz, 2H), 2.62 (t, J=7.5 Hz, 2H), 2.61 (t, J=6.9 Hz, 2H), 2.37 (s, 3H), 1.90 (m, 2H).

EXAMPLE 2(8)

3-(5-(2-(2-(4-Methoxyphenyl)-5-methyloxazol-4-yl)ethoxy)-1,2,3,4-tetrahydroquinolin-1-yl)propanoic acid

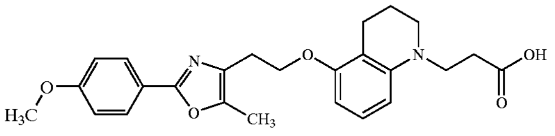

TLC: Rf 0.78 (hexane:ethyl acetate=1:10);

NMR ($CDCl_3$): δ 7.91 (d, J=9.0 Hz, 2H), 7.00 (dd, J=8.4, 7.8 Hz, 1H), 6.94 (d, J=9.0 Hz, 2H), 6.32 (d, J=8.4 Hz, 1H), 6.30 (d, J=7.8 Hz, 1H), 4.20 (t, J=6.6 Hz, 2H), 3.85 (s, 3H), 3.59 (t, J=7.2 Hz, 2H), 3.21 (t, J=5.4 Hz, 2H), 2.95 (t, J=6.6 Hz, 2H), 2.62 (t, J=7.2 Hz, 4H), 2.35 (s, 3H), 1.90 (m, 2H).

EXAMPLE 2(9)

3-(5-(2-(2-(4-t-Butylphenyl)-5-methyloxazol-4-yl)ethoxy)-1,2,3,4-tetrahydroquinolin-1-yl)propanoic acid

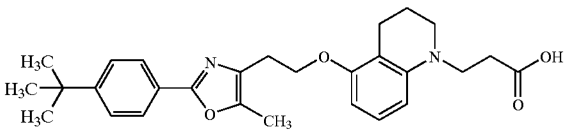

TLC: Rf 0.76 (hexane:ethyl acetate=1:10);

NMR ($CDCl_3$): δ 7.81 (d, J=8.7 Hz, 2H), 7.36 (d, J=8.7 Hz, 2H), 6.90 (dd, J=8.7, 8.4 Hz, 1H), 6.23 (d, J=8.7 Hz, 1H), 6.18 (d, J=8.4 Hz, 1H), 4.11 (t, J=6.3 Hz, 2H), 3.52 (t, J=6.9 Hz, 2H), 3.12 (t, J=5.4 Hz, 2H), 2.89 (t, J=6.3 Hz, 2H), 2.53 (t, J=6.9 Hz, 4H), 2.27 (s, 3H), 1.80 (m, 2H), 1.25 (s, 9H).

EXAMPLE 2(10)

3-(5-(2-(2-(4-Fluorophenyl)-5-methyloxazol-4-yl)ethoxy)-1,2,3,4-tetrahydroquinolin-1-yl)propanoic acid

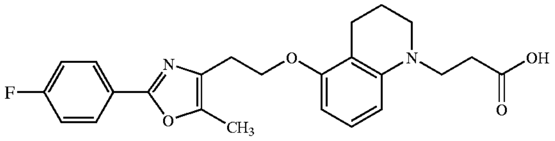

TLC: Rf 0.86 (hexane:ethyl acetate=1:10);

NMR ($CDCl_3$): δ 7.97 (d, J=8.7 Hz, 1H), 7.95 (d, J=9.0 Hz, 1H), 7.12 (d, J=9.0 Hz, 1H), 7.09 (d, J=8.7 Hz, 1H), 7.00 dd, J=8.4, 8.1 Hz, 1H), 6.32 (d, J=8.4 Hz, 1H), 6.29 (d, J=8.1 Hz, 1H), 4.20 (t, J=6.3 Hz, 2H), 3.59 (t, J=7.2 Hz, 2H), 3.21 (t, J=5.4 Hz, 2H), 2.95 (t, J=6.3 Hz, 2H), 2.62 (t, J=7.2 Hz, 4H), 2.36 (s, 3H), 1.90 (m, 2H).

EXAMPLE 2(11)

3-(5-(2-(2-(4-Propylphenyl)-5-methyloxazol-4-yl)ethoxy)-1,2,3,4-tetrahydroquinolin-1-yl)propanoic acid

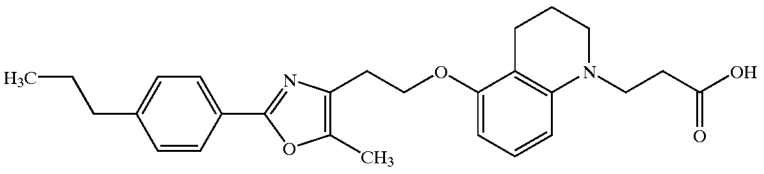

TLC: Rf 0.44 (chloroform:methanol=10:1);

NMR ($CDCl_3$): δ 7.87 (d, J=8.4 Hz, 2H), 7.23 (d, J=8.4 Hz, 2H), 6.98 (dd, J=8.1, 8.1 Hz, 1H), 6.29 (m, 2H), 4.19 (t, J=6.6 Hz, 2H), 3.57 (t, J=6.6 Hz, 2H), 3.19 (m, 2H), 2.95 (t, J=6.6 Hz, 2H), 2.61 (m, 6H), 2.34 (s, 3H), 1.88 (m, 2H), 1.66 (m, 2H), 0.93 (t, J=7.2 Hz, 3H).

REFERENCE EXAMPLE 6

5-Acetyloxyquinoline

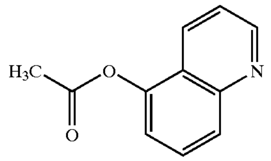

To a solution of 5-hydroxyquinoline (5.1 g) in pyridine (100 ml) was added acetic anhydride (4.0 ml) and then the reaction mixture was stirred at room temperature for 3 days. The reaction mixture was concentrated. The residue was diluted with water. The diluted solution was extracted with ethyl acetate. The extracted solution was washed with water and a saturated aqueous solution of sodium chloride subsequently, dried over anhydrous magnesium sulfate and then concentrated. The residue was azeotropled with toluene to give the title compound (7.7 g) having the following physical data. The obtained compound was used without purification in the subsequent reaction.

TLC: Rf 0.27 (hexane:ethyl acetate=2:1).

REFERENCE EXAMPLE 7

5-Acetyloxy-1,2,3,4-tetrahydroquinoline

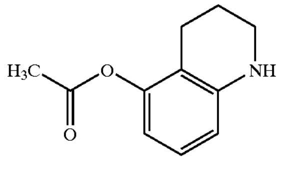

To a solution of the compound (7.7 g) prepared in reference example 6 in methanol (50 ml) was added platinum dioxide (500 mg) under an atmosphere of argon. The atmosphere was substituted with hydrogen. The reaction mixture was stirred at room temperature overnight. The reaction mixture was filtered using cellite. The filtrate was concentrated. The residue was purified by column chromatography on silica gel (hexane:ethyl acetate=4:1→3:1) to give the title compound (6.6 g) having the following physical data.

TLC: Rf 0.50 (hexane:ethyl acetate=2:1);

NMR ($CDCl_3$): δ 6.94 (dd, J=8.1, 8.1 Hz, 1H), 6.34 (m, 2H), 3.26 (t, J=5.4 Hz, 2H), 2.55 (t, J=6.6 Hz, 2H), 2.28 (s, 3H), 1.91 (m, 2H).

REFERENCE EXAMPLE 8

5-Acetyloxy-1-(2-cyanoethyl)-1,2,3,4-tetrahydroquinoline

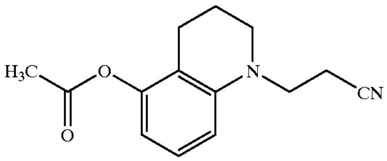

To a solution of the compound (5.3 g) prepared in reference example 7 in acrylonitrile (10 ml) was added copper(I) chloride (1.4 g) and acetic acid (0.8 ml). The reaction mixture was refluxed overnight under an atmosphere of argon. After the reaction mixture was cooled to room temperature, to the reaction mixture was added 28% ammonia water in order to make it alkalinity. The solution was diluted with water and then extracted with ethyl acetate. The extraction was washed with water and a saturated aqueous solution of sodium chloride subsequently, dried over anhydrous magnesium sulfate and then concentrated. The residue was purified by column chromatography on silica gel (hexane:ethyl acetate=3:1→2:1) to give the title compound (6.1 g) having the following physical data.

TLC: Rf 0.43 (hexane:ethyl acetate=2:1);

NMR ($CDCl_3$): δ 7.06 (dd, J=8.1, 8.1 Hz, 1H), 6.40 (m, 2H), 3.65 (t, J=6.6 Hz, 2H), 3.35 (t, J=5.4 Hz, 2H), 2.59 (m, 4H), 2.29 (s, 3H), 1.94 (m, 2H).

REFERENCE EXAMPLE 9

5-Hydroxy-1-(2-cyanoethyl)-1,2,3,4-tetrahydroquinoline

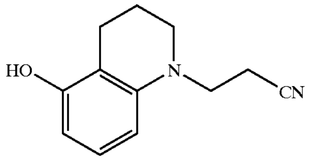

To a solution of the compound (6.1 g) prepared in reference example 8 in ethanol (150 ml) was added 2N aqueous solution of sodium hydroxide (15 ml) and the mixture was stirred at room temperature overnight. The reaction mixture was reutilized with 2N hydrochloric acid and then concentrated. The residue was diluted with water and extracted with ethyl acetate. The extraction was washed with water and a saturated aqueous solution of sodium chloride, dried over anhydrous magnesium sulfate and concentrated. The residue was purified by column chromatography on silica gel (hexane:ethyl acetate=1:1) to give the title compound (4.5 g) having the following physical data.

TLC: Rf 0.61 (hexane:ethyl acetate 1:1);

NMR ($CDCl_3$): δ 6.93 (dd, J=8.1, 8.1 Hz, 1H), 6.19 (d, J=8.1 Hz, 1H), 6.14 (d, J=8.1 Hz, 1H), 4.78 (s, 1H), 3.64 (t, J=7.2 Hz, 2H), 3.34 (t, J=6.0 Hz, 2H), 2.66 (t, J=6.0 Hz, 2H), 2.59 (t, J=7.2 Hz, 2H), 1.99 (m, 2H).

REFERENCE EXAMPLE 10

3-(5-(2-(2-(1,2,5,6-Tetrahydropyridin-1-yl)-5-methylthiazol-4-yl)ethoxy)-1,2,3,4-tetrahydroquinolin-1-yl)propanenitrile

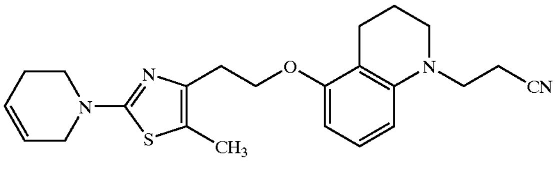

To a solution of 2-(2-(1,2,5,6-tetrahydropyridin-1-yl)-5-methylthiazol-4-yl)ethanol (1.79 g), the compound (800 mg) prepared in reference example 9 and triphenylphosphine (2.10 g) in methylene chloride was added 1,1'-(azodicarbonyl)dipiperidine (2.02 g) under an atmosphere of argon and the mixture was stirred at room temperature for 4 hours. The reaction mixture was concentrated. The residue was diluted with diethyl ether and then filtered. The filtrate was washed with 2N aqueous solution of sodium hydroxide (20 ml), water (100 ml) and a saturated aqueous solution of sodium chloride subsequently, dried over anhydrous magnesium sulfate and then concentrated. The residue was purified by column chromatography on silica gel (hexane:ethyl acetate=5:1) to give the title compound (1.55 g) having the following physical data.

TLC: Rf 0.55 (hexane:ethyl acetate=1:1);

NMR ($CDCl_3$): δ 7.00 (dd, J=8.4, 8.1 Hz, 1H), 6.30 (d, J=8.4 Hz, 1H), 6.18 (d, J=8.1 Hz, 1H), 5.92–5.82 (m, 1H), 5.78–5.70 (m, 1H), 4.18 (t, J=6.6 Hz, 2H), 3.88–3.81 (m, 2H), 3.64 (t, J=6.9 Hz, 2H), 3.54 (t, J=5.7 Hz, 2H), 3.31–3.27 (m, 2H), 2.94 (t, J=6.6 Hz, 2H), 2.63 (t, J=6.6 Hz, 2H), 2.58 (t, J=6.9 Hz, 2H), 2.31–2.20 (m, 2H), 2.26 (s, 3H), 1.99–1.87 (m, 2H).

EXAMPLE 3

3-(5-(2-(2-(1,2,5,6-Tetrahydropyridin-1-yl)-5-methylthiazol-4-yl)ethoxy)-1,2,3,4-tetrahydroquinolin-1-yl)propanoic acid dihydrochloride

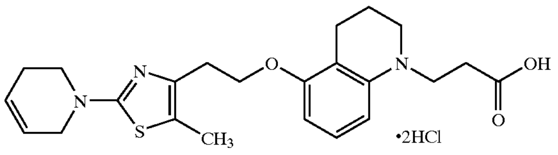

To a solution of the compound (1.16 g) prepared in reference example in ethanol (30 ml) was added 5N aqueous solution of sodium hydroxide (5.00 ml) and the mixture was stirred at 80° C. for 15 hours. To the reaction mixture was added 2N hydrochloric acid in order to adjust the pH to 5. The mixture was extracted with ethyl acetate. The extraction was washed with water and a saturated aqueous solution of sodium chloride, dried over anhydrous magnesium sulfate and then concentrated. To the solution of the residue in ethyl acetate (10 ml) was added 4N hydrochloric acid in ethyl acetate (5 ml) and the mixture was stirred at room temperature for 5 minutes. The reaction mixture was diluted with diethyl ether and then filtered to give the compound of the present invention (1.33 g) having the following physical data.

TLC: Rf 0.44 (chloroform:methanol=9:1);

NMR (DMSO-$d_6$): δ 6.96 (t, J=8.1 Hz; 1H), 6.36 (d, J=8.1 Hz, 1H) 6.29 (d, J=8.4 Hz, 1H), 5.99–5.90 (m, 1H), 5.80–5.75 (m, 1H), 5.60–3.80 (br, 1H), 4.16 (t, J=5.7 Hz, 2H), 4.09 (brs, 2H), 3.77 (t, J=5.7 Hz, 2H), 3.48 (t, J=6.9 Hz, 2H), 3.16 (t, J=5.4 Hz, 2H), 3.06 (t, J=5.7 Hz, 2H), 2.55–2.45 (m, 2H), 2.45 (t, J=6.9 Hz, 2H), 2.34–2.20(m, 2H), 2.22 (s, 3H), 1.84–1.72 (m, 2H).

EXAMPLE 4(1) TO EXAMPLE 4(4)

The following compounds of the present invention were obtained in the same manner as in Reference Example 10→Example 3 (the procedure converted into hydrochloride was not performed) using a corresponding compounds instead of 2-(2-(1,2,5,6-tetrahydropyridin-1-yl)-5-methylthiazol-4-yl)ethanol and using the compound prepared in Example 9 or a corresponding derivatives instead of it.

EXAMPLE 4(1)

3-(5-(2-(2-(4-Methylthiophenyl)-5-methyloxazol-4-yl)ethoxy)-1,2,3,4-tetrahydroquinolin-1-yl)propanoic acid

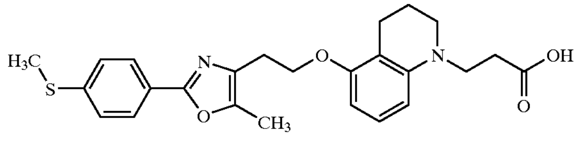

TLC: Rf 0.32 (chloroform:methanol=9:1);

NMR ($CDCl_3$): δ 7.87 (d, J=8.4 Hz, 2H), 7.27 (m, 2H), 7.00 (t, J=8.4 Hz, 1H), 6.31 (t, J=9.0 Hz, 2H), 4.20 (t, J=6.6 Hz, 2H), 3.59 (t, J=7.2 Hz, 2H), 3.21 (t, J=5.4 Hz, 2H), 2.95 (t, J=6.6 Hz, 2H), 2.62 (m, 4H), 2.52 (s, 3H), 2.36 (s, 3H), 1.90 (m, 2H).

EXAMPLE 4(2)

3-(7-(2-(2-(4-Methylphenyl)-5-methyloxazol-4-yl)ethoxy)-1,2,3,4-tetrahydroquinolin-1-yl)propanoic acid

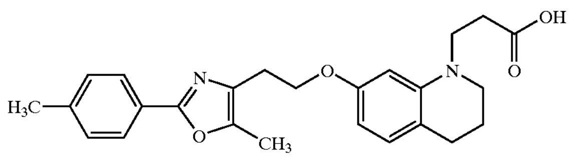

TLC: Rf 0.47 (chloroform:methanol=9:1);

NMR ($CDCl_3$) δ 7.85 (d, J=8.7 Hz, 2H), 7.24 (d; J=8.37 Hz, 2H), 6.82 (d, J=7.8 Hz; 1H), 6.53 (d, J=2.1 Hz, 1H), 6.18 (dd, J=7.8, 2.1 Hz, 1H), 4.25 (t, J=8.1 Hz, 2H), 3.69 (t, J=5.7 Hz, 2H), 3.26 (t, J=5.4 Hz, 2H), 2.90 (t, J=8.1 Hz, 2H), 2.68 (t, J=6.6 Hz, 2H), 2.60 (t, J=5.7 Hz, 2H), 2.39 (s, 3H), 2.36 (s, 3H), 1.93 (m, 2H).

EXAMPLE 4(3)

3-(6-(2-(2-(4-Methylphenyl)-5-methyloxazol-4-yl)ethoxy)-1,2,3,4-tetrahydroquinolin-1-yl)propanoic acid

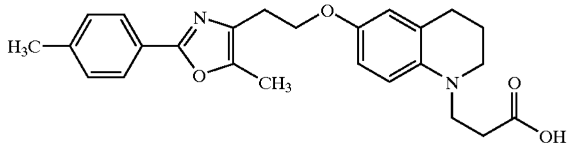

TLC: Rf 0.32 (chloroform:methanol=9:1);

NMR ($CDCl_3$): δ 7.86 (d, J=8.1 Hz, 2H), 7.23 (d, J=8.1 Hz, 2H), 6.67 (d, J=2.1 Hz, 2H), 6.60 (s, 1H), 4.16 (t, J=6.9 Hz, 2H), 3.50 (t, J=6.9 Hz, 2H), 3.18 (t, J=5.4 Hz, 2H), 2.93 (t, J=6.9 Hz, 2H), 2.73 (t, J=6.9 Hz, 2H), 2.62 (t, J=6.9 Hz, 2H), 2.38 (s, 3H), 2.36 (s, 3H), 1.92 (m, 2H).

EXAMPLE 4(4)

3-(5-(2-(2-(6-Dimethylaminopyridin-3-yl)-5-methyloxazol-4-yl)ethoxy)-1,2,3,4-tetrahydroquinolin-1-yl)propanoic acid

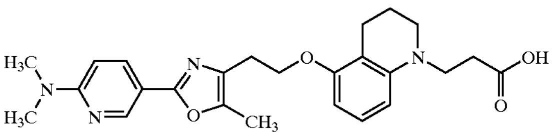

TLC: Rf 0.29 (chloroform:methanol=10:1);

NMR ($CDCl_3$): δ 8.72 (d, J=2.4 Hz, 1H), 7.98 (dd, J=9.0, 2.4 Hz, 1H), 6.99 (t, J=7.8 Hz, 1H), 6.53 (d, J=9.0 Hz, 1H), 6.31 (t, J=9.0 Hz, 2H), 4.19 (t, J=6.6 Hz, 2H), 3.59 (t, J=6.6 Hz, 2H), 3.49 (s, 1H), 3.21 (t, J=5.4 Hz, 2H), 3.15 (s, 6H), 2.94 (t, J=6.6 Hz, 2H), 2.62 (t, J=6.9 Hz, 4H), 2.34 (s, 3H), 1.89 (m, 2H).

EXAMPLE 5

5-(2-(2-(4-Chlorophenyl)-5-methyloxazol-4-yl)ethoxy)-1-(2-(1H-tetrazol-5-yl)ethyl)-1,2,3,4-tetrahydroquinoline

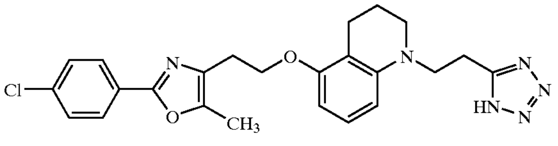

A solution of 3-(5-(2-(2-(1,2,5,6-tetrahydropyridin-1-yl)-5-methylthiazol-4-yl)ethoxy)-1,2,3,4-tetrahydroquinolin-1-yl)propanenitrile (421 mg; it was obtained in the same manner as in Reference Example 10 using 2-(2-(4-chlorophenyl)-5-methyloxazol-4-yl)ethanol instead of 2-(2-(1,2,5,6-tetrahydropyridin-1-yl)-5-methylthiazole)ethanol) and trimethyltin azide (617 mg) in anhydrous toluene (10 ml) was stirred at room temperature for 48 hours under an atmosphere of argon. The reaction mixture was concentrated. The residue was diluted with methanol (20 ml). To the solution was added 1N hydrochloric acid (10 ml) and the mixture was stirred at room temperature for 1 hour. The reaction mixture was extracted with ethyl acetate. The extraction was washed with a saturated aqueous solution of sodium chloride, dried over anhydrous magnesium sulfate and then concentrated. The residue was purified by column chromatography on silica gel (ethyl acetate) to give the compound of the present invention (300 mg) having the following physical data.

TLC: Rf 0.37 (chloroform:methanol=9:1);

NMR (DMSO-$d_6$): δ 7.90 (d, J=8.7 Hz, 2H), 7.55 (d, J=8.7 Hz, 2H), 6.91 (dd, J=8.4, 8.4 Hz, 1H), 6.29 (d, J=8.4 Hz, 1H), 6.25 (d, J=8.4 Hz, 1H), 4.11 (t, J=6.3 Hz, 2H), 3.60 (t, J=6.9 Hz, 2H), 3.10–3.01 (m, 4H), 2.89 (t, J=6.3 Hz, 2H), 2.50–2.40 (m, 2H), 2.34 (s, 3H), 1.75–1.65 (m, 2H).

EXAMPLE 6(1) TO EXAMPLE 6(3)

The following compounds of the present invention were obtained in the same manner as in Reference Example 5→Example 5 using a corresponding derivatives instead of 2-(2-(1,2,5,6-tetrahydropyridin-1-yl)-5-methylthiazol-4-yl)ethanol.

EXAMPLE 6(1)

5-(2-(2-(4-Trifluoromethylphenyl)-5-methyloxazol-4-yl)ethoxy)-1-(2-(1H-tetrazol-5-yl)ethyl)-1,2,3,4-tetrahydroquinoline

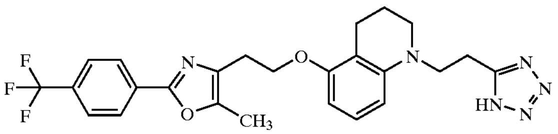

TLC: Rf 0.60 (ethyl acetate);

NMR (DMSO-$d_6$): δ 8.10 (d, J=8.5 Hz, 2H), 7.85 (d, J=8.5 Hz, 2H), 6.91 (t, J=8.5 Hz, 1H), 6.32–6.23 (m, 2H), 4.13 (t, J=6.0 Hz, 2H), 3.64–3.57 (m, 2H), 3.10–3.03 (m, 4H), 2.92 (t, J=6.0 Hz, 2H), 2.45 (t, J=6.0 Hz, 2H), 2.37 (s, 3H), 1.76–1.66 (m, 2H).

EXAMPLE 6(2)

5-(2-(2-(4-Fluorophenyl)-5-methyloxazol-4-yl)ethoxy)-1-(2-(1H-tetrazol-5-yl)ethyl)-1,2,3,4-tetrahydroquinoline

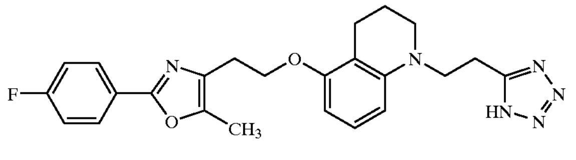

TLC: Rf 0.64 (ethyl acetate);

NMR (DMSO-$d_6$): δ 7.94 (dd, J=9.0, 5.5 Hz, 2H), 7.32 (t, J=9.0 Hz, 2H), 6.91 (t, J=8.5 Hz, 1H), 6.29 (d, J=8.5 Hz, 1H), 6.25 (d, J=8.5 Hz, 1H), 4.11 (t, J=6.5 Hz, 2H), 3.64–3.57 (m, 2H), 3.10–3.03 (m, 4H), 2.88 (t, J=6.5 Hz, 2H), 2.45 (t, J=6.5 Hz, 2H), 2.33 (s, 3H), 1.76–1.66 (m, 2H).

EXAMPLE 6(3)

5-(2-(2-(4-Methylphenyl)-5-methyloxazol-4-yl)ethoxy)-1-(2-(1H-tetrazol-5-yl)ethyl)-1,2,3,4-tetrahydroquinoline

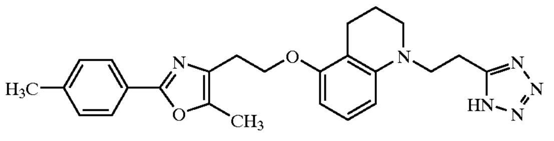

TLC: Rf 0.38 (chloroform:methanol=1:1);

NMR (DMSO-$d_6$): δ 7.79 (d, J=8.4 Hz, 2H), 7.29 (d, J=8.4 Hz, 2H), 6.91 (dd, J=8.1, 8.1 Hz, 1H), 6.29 (d, J=8.1 Hz, 1H), 6.25 (d, J=8.1 Hz, 1H), 4.11 (t, J=6.3 Hz, 2H), 3.61 (dd, J=7.5, 7.5 Hz, 2H), 3.12–3.02 (m, 4H), 2.87 (t, J=6.3 Hz, 2H), 2.46 (t, J=6.6 Hz, 2H), 2.34 (s, 3H), 2.32 (s, 3H), 1.71 (m, 2H).

EXAMPLE 7(1) TO EXAMPLE 7(4)

The following compounds of the present invention were obtained in the same manner as in Example 1 using the compound prepared in Reference Example 5 or a corresponding derivatives instead of it and using 2-(5-methyl-2-(4-methylphenyl)oxazol-4-yl)ethanol or a corresponding derivatives instead of it.

EXAMPLE 7(1)

3-(5-(2-(2-(4-Cyanophenyl)-5-methyloxazol-4-yl)ethoxy)-1,2,3,4-tetrahydroquinolin-1-yl)propanoic acid methyl ester

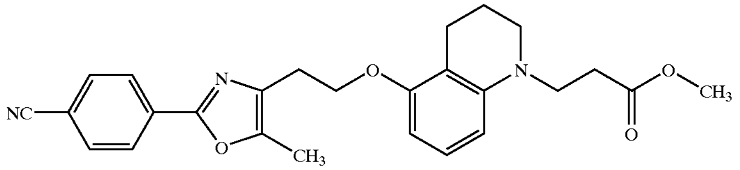

TLC: Rf 0.37 (hexane:ethyl acetate=1:1);

NMR ($CDCl_3$): δ 7.99 (d, J=8.7 Hz, 2H), 7.64 (d, J=8.7 Hz, 2H), 6.92 (dd, J=8.4, 8.1 Hz, 1H), 6.21 (d, J=8.4 Hz, 1H), 6.17 (d, J=8.4 Hz, 1H), 4.13 (t, J=6.3 Hz, 2H), 3.60 (s, 3H), 3.52 (t, J=7.5 Hz, 2H), 3.13 (t, J=5.4 Hz, 2H), 2.89 (t, J=6.3 Hz, 2H), 2.52 (t, J=7.5 Hz, 2H), 2.50 (t, J=6.3 Hz, 2H), 2.32 (s, 3H), 1.81 (m, 2H).

EXAMPLE 7(2)

4-(5-(2-(2-(4-Methylphenyl)-5-methyloxazol-4-yl)ethoxy)-1,2,3,4-tetrahydroquinolin-1-yl)butanoic acid ethyl ester

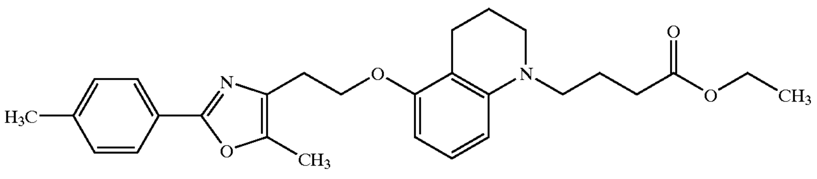

TLC: Rf 0.63 (hexane:ethyl acetate=1:1);

NMR ($CDCl_3$): δ 7.86 (d, J=8.1 Hz, 2H), 7.22 (d, J=8.1 Hz, 2H), 6.90 (m, 1H), 6.18 (m, 2H), 4.22 (t, J=6.6 Hz, 2H), 4.13 (q, J=7.2 Hz, 2H), 3.80 (t, J=6.9 Hz, 1H), 3.69 (t, J=6.9 Hz, 1H), 3.21 (m, 4H), 2.95 (t, J=7.2 Hz, 2H), 2.62 (t, J=6.6 Hz, 2H), 2.38 (s, 3H), 2.36 (m, 2H), 2.35 (s, 2H), 1.88 (m, 2H), 1.25 (t, J=7.2 Hz, 3H).

EXAMPLE 7(3)

5-(5-(2-(2-(4-Methylphenyl)-5-methyloxazol-4-yl)ethoxy)-1,2,3,4-tetrahydroquinolin-1-yl)pentanoic acid ethyl ester

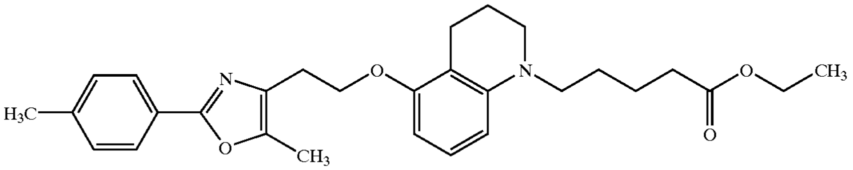

TLC: Rf 0.54 (hexane:ethyl acetate=2:1);

NMR ($CDCl_3$): δ 7.85 (d, J=8.4 Hz, 2H), 7.22 (d, J=8.4 Hz, 2H), 6.96 (dd, J=8.4, 8.1 Hz, 1H), 6.28 (d, J=8.4 Hz, 1H), 6.22 (d, J=8.1 Hz, 1H), 4.20 (t, J=6.6 Hz, 2H), 4.12 (q, J=7.2 Hz, 2H), 3.26 (t, J=7.2 Hz, 2H), 3.19 (t, J=5.4 Hz, 2H), 2.95 (t, J=6.6 Hz, 2H), 2.62 (t, J=6.6 Hz, 2H), 2.38 (s, 3H), 2.33 (m, 2H), 1.89 (m, 4H), 1.62 (m, 2H), 1.25 (t, J=7.2 Hz, 3H).

EXAMPLE 7(4)

2-(5-(2-(2-(4-Methylphenyl)-5-methyloxazol-4-yl)ethoxy)-1,2,3,4-tetrahydroquinolin-1-yl)acetic acid ethyl ester

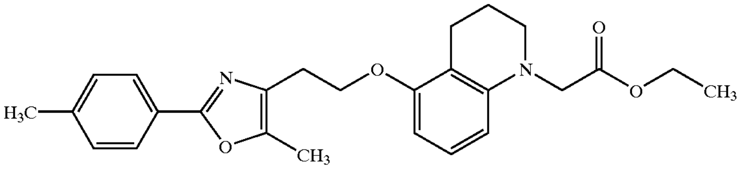

TLC: Rf 0.64 (hexane:ethyl acetate=1:2);

NMR ($CDCl_3$): δ 7.86 (d, J=8.4 Hz, 2H), 7.22 (d, J=8.4 Hz, 2H), 6.94 (t, J=8.1 Hz, 1H), 6.28 (d, J=8.1 Hz, 1H), 6.09 (d, J=8.1 Hz, 1H), 4.20 (t, J=6.6 Hz, 2H), 4.16 (q, J=7.2 Hz, 2H), 3.97 (s, 2H), 3.33 (t, J=5.7 Hz, 2H), 2.95 (t, J=6.6 Hz, 2H), 2.66 (t, J=6.6 Hz, 2H), 2.38 (s, 3H), 2.35 (s, 3H), 1.94 (m, 2H), 1.23 (t, J=7.2 Hz, 3H).

EXAMPLE 8(1) TO EXAMPLE 8(4)

The following compounds of the present invention were obtained in the same manner as in Example 1 using the compound prepared in Example 7(1) to 7(4) instead of the compound prepared in Example 1.

EXAMPLE 8(1)

3-(5-(2-(2-(4-Cyanophenyl)-5-methyloxazol-4-yl)ethoxy)-1,2,3,4-tetrahydroquinolin-1-yl)propanoic acid

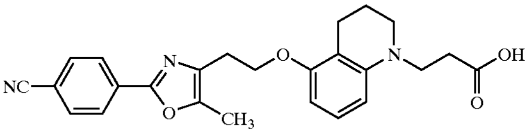

TLC: Rf 0.41 (chloroform:methanol=9:1);

NMR ($CDCl_3$): δ 8.07 (d, J=9.0 Hz, 2H), 7.71 (d, J=9.0 Hz, 2H), 7.00 (t, J=8.4 Hz, 1H), 6.31 (d, J=8.4 Hz, 1H), 6.27 (d, J=8.4 Hz, 1H), 4.21 (t, J=6.3 Hz, 2H), 3.60 (t, J=7.2 Hz, 2H), 3.21 (t, J=5.4 Hz, 2H), 2.97 (t, J=6.3 Hz, 2H), 2.61 (m, 4H), 2.39 (s, 3H), 1.89 (m, 2H).

EXAMPLE 8(2)

4-(5-(2-(2-(4-Methylphenyl)-5-methyloxazol-4-yl)ethoxy)-1,2,3,4-tetrahydroquinolin-1-yl)butanoic acid

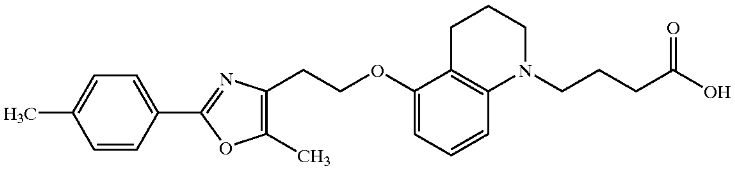

TLC: Rf 0.66 (chloroform methanol=10:1);

NMR ($CDCl_3$): δ 7.85 (d, J=8.1 Hz, 2H), 7.22 (d, J=8.1 Hz, 2H), 6.96 (t, J=8.1 Hz, 1H), 6.28 (d, J=8.1 Hz, 1H), 6.23 (d, J=8.1 Hz, 1H), 4.19 (t, J=6.6 Hz, 2H), 3.28 (t, J=7.2 Hz, 2H), 3.19 (t, J=5.7 Hz, 21), 2.95 (t, J=6.6 Hz, 2H), 2.62 (t, J=6.6 Hz, 2H), 2.41 (t, J=7.2 Hz, 2H), 2.38(s, 3H), 2.35 (s, 3H), 1.88 (m, 4H).

EXAMPLE 8(3)

5-(5-(2-(2-(4-Methylphenyl)-5-methyloxazol-4-yl)ethoxy)-1,2,3,4-tetrahydroquinolin-1-yl)pentanoic acid

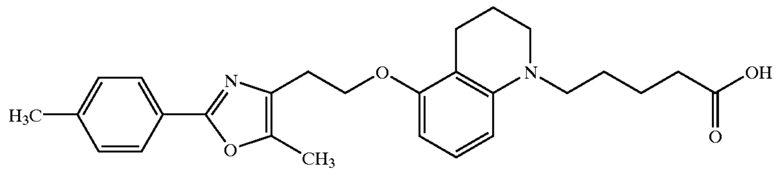

TLC: Rf 0.78 (chloroform:methanol=10:1);

NMR ($CDCl_3$): δ 7.85 (d, J=8.4 Hz, 211), 7.22 (d, J=8.4 Hz, 2H), 6.96 (t, J=8.1 Hz, 1H), 6.23 (t, J=8.1 Hz, 2H), 4.19 (t, J=6.6 Hz, 2H), 3.24 (t, J=7.2 Hz, 2H), 3.19 (t, J=5.7 Hz, 2H), 2.95 (t, J=6.6 Hz, 2H), 2.62 (t, J=6.6 Hz, 2H), 2.39 (m, 2H), 2.38 (s, 3H), 2.35 (s, 3H), 1.88 (m, 2H), 1.65 (m, 4H).

EXAMPLE 8(4)

2-(5-(2-(2-(4-Methylphenyl)-5-methyloxazol-4-yl)ethoxy)-1,2,3,4-tetrahydroquinolin-1-yl)acetic acid

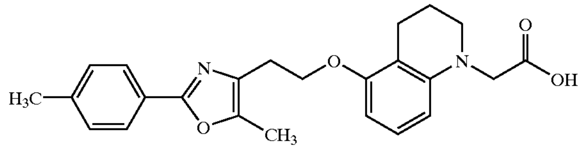

TLC: Rf 0.55 (chloroform:methanol=10:1);

NMR ($CDCl_3$): δ 7.85 (d, J=8.1 Hz, 2H), 7.22 (d, J=8.1 Hz, 2H), 6.98 (dd, J=8.4, 8.1 Hz, 2H), 6.33 (d, J=8.1 Hz, 1H), 6.14 (d, J=8.4 Hz, 1H), 4.19 (t, J=6.6 Hz, 2H), 3.96 (s, 2H), 3.30 (t, J=5.7 Hz, 2H), 2.95 (t, J=6.16 Hz, 2H), 2.67 (t, J=6.6 Hz, 2H), 2.38 (s, 3H), 2.35 (s, 3H), 1.96 (m, 2H).

EXAMPLE 9

3-(5-(2-(2-(4-Methylphenyl)-5-methyloxazol-4-yl)ethoxy)-1,2,3,4-tetrahydroquinolin-1-yl)propanoic acid sodium salt

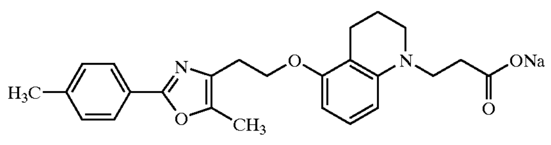

To a solution of the compound (100 ml) prepared in Example 2 in ethanol (2 ml) was added 1N aqueous solution of sodium hydroxide (0.23 ml) and the mixture was stirred at room temperature for 10 minutes. The reaction mixture was concentrated to give the compound of the present invention (73 mg) having the following physical data.

TLC: Rf 0.51 (chloroform:methanol=10:1);

NMR (DMSO-$d_6$): δ 7.78 (d, J=8.0 Hz, 2H), 7.29 (d, J=8.0 Hz, 2H), 6.86 (t, J=8.0 Hz, 1H), 6.23 (d, J=8.0 Hz, 1H), 6.16 (d, J=8.0 Hz, 1H), 4.09 (t, J=6.5 Hz, 2H), 3.41–3.33 (m, 2H), 3.14–3.09 (m, 2H), 2.86 (t, J=6.5 Hz, 2H), 2.45 (t, J=6.5 Hz, 2H), 2.34 (s, 3H), 2.32 (s, 3H), 2.08–2.01 (m, 2H), 1.79–1.69 (m, 2H).

EXAMPLE 9(1) TO EXAMPLE 9(3)

The following compounds of the present invention were obtained in the same manner as in Example 9 using the compound prepared in Example 2(2), 2(5) and 2(10) instead of the compound prepared in Example 2.

EXAMPLE 9(1)

3-(5-(2-(2-(4-Trifluoromethylphenyl)-5-methyloxazol-4-yl)ethoxy)-1,2,3,4-tetrahydroquinolin-1-yl)propanoic acid sodium salt

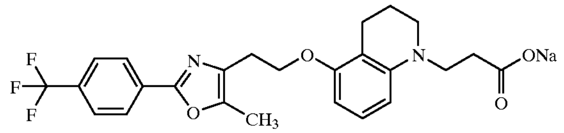

TLC: Rf 0.47 (hexane:ethyl acetate=1:1);

NMR (DMSO-$d_6$): δ 8.09 (d, J=8.4 Hz, 2H), 7.84 (d, J=8.4 Hz, 2H), 6.83 (dd, J=8.7, 8.1 Hz, 1H), 6.24 (d, J=8.7 Hz, 1H), 6.16 (d, J=8.4 Hz, 1H), 4.11 (t, J=6.3 Hz, 2H), 3.50–3.30 (m, 2H), 3.11 (t, J=5.4 Hz, 2H), 2.90 (t, J=6.3 Hz, 2H), 2.44 (t, J=6.3 Hz, 2H), 2.36 (s, 3H), 2.05 (t, J=7.5 Hz, 2H), 1.78–1.58 (m, 2H).

EXAMPLE 9(2)

3-(5-(2-(2-(4-Chlorophenyl)-5-methyloxazol-4-yl)ethoxy)-1,2,3,4-tetrahydroquinolin-1-yl)propanoic acid sodium salt

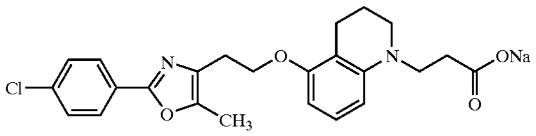

TLC: Rf 0.57 (chloroform:methanol=10:1);

NMR ($CD_3OD$): δ 7.92 (d, J=8.7 Hz, 2H), 7.47 (d, J=8.7 Hz, 2H), 6.90 (t, J=8.1 Hz, 1H), 6.38 (d, J=8.1 Hz, 1H), 6.21 (d, J=8.1 Hz, 1H), 4.18 (t, J=6.6 Hz, 2H), 3.53 (t, J=7.5 Hz, 2H), 3.20 (t, J=5.4 Hz, 2H), 2.93 (t, J=6.6 Hz, 2H), 2.51 (t, J=6.6 Hz, 2H), 2.38 (t, J=7.5 Hz, 2H), 2.33 (s, 3H), 1.82 (quint., J=5.4 Hz, 2H).

EXAMPLE 9(3)

3-(5-(2-(2-(4-Fluorophenyl)-5-methyloxazol-4-yl)ethoxy)-1,2,3,4-tetrahydroquinolin-1-yl)propanoic acid sodium salt

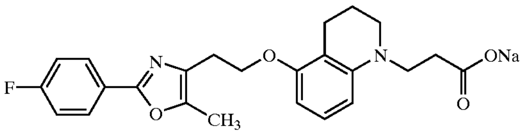

TLC: Rf 0.76 (chloroform:methanol=10:1);

NMR ($CD_3OD$): δ 7.96 (dd, J=9.0, 8.7 Hz, 2H), 7.18 (dd, J=9.0, 8.7 Hz, 2H), 6.90 (dd, J=8.4, 8.1 Hz, 1H), 6.38 (d, J=8.1 Hz, 1H), 6.20 (d, J=8.4 Hz, 1H), 4.16 (t, J=6.3 Hz, 2H), 3.53 (t, J=7.8 Hz, 2H), 3.20 (t, J=5.4 Hz, 2H), 2.91 (t, J=6.3 Hz, 2H), 2.51 (t, J=6.3 Hz, 2H), 2.38 (t, J=7.8 Hz, 2H), 2.31 (s, 3H), 1.82 (quint., J=5.4 Hz, 2H).

FORMULATION EXAMPLE 1

The following components were admixed in a conventional method and punched out to obtain 100 tablets each containing 50 mg of the active ingredient.

| | |
|---|---|
| 3-(5-(2-(2-(4-methylphenyl)-5-methyloxazol-4-yl)ethoxy)-1,2,3,4-tetrahydroquinoline-1-yl)propanoic acid | 5.0 g |
| Carboxymethyl cellulose calcium (disintegrating agent) | 0.2 g |
| Magnesium stearate (lubricant) | 0.1 g |
| Microcrystalline cellulose | 4.7 g |

FORMULATION EXAMPLE 2

The following components were admixed in a conventional method, and the solution was sterilized in a conventional method, placed at 5 ml into ampoules and freeze-dried in a conventional method to thereby obtain 100 ampoules each containing 20 mg of the active ingredient.

| | |
|---|---|
| 3-(5-(2-(2-(4-methylphenyl)-5-methyloxazol-4-yl)ethoxy)-1,2,3,4-tetrahydroquinoline-1-yl)propanoic acid | 2.0 g |
| Mannitol | 20 g |
| Distilled water | 1000 ml |

What is claimed is:

1. A tetrahydroquinoline compound represented by formula (I)

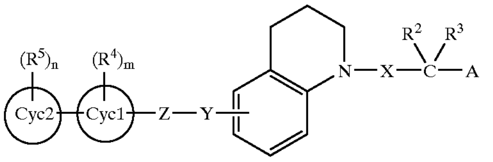

wherein

A represents (1) —COOR', or (2) 1H-tetrazol-5-yl, $R^1$ represents (1) hydrogen atom, or (2) C1–10 alkyl, $R^2$ and $R^3$ each independently represents (1) hydrogen atom, or (2) C1–10 alkyl, or taken together with the carbon atom to which they are attached, represents C3–7 cycloalkylene, X represents (1) bond, or (2) C1–3 alkylene, Y represents (1) —O—, or (2) —S—, Z represents C1–4 alkylene, Cyc1 and Cyc2 each independently represents (1) partially or fully optionally saturated C3–15 mono-, bi-, or tricarbocyclic aryl, or (2) partially or fully optionally saturated 3–15 membered mono-, bi- or triheterocyclic aryl containing 1–4 hetero atom(s) selected from oxygen, nitrogen or sulfur atom, $R^4$ and $R^5$ each independently represents (1) C1–10 alkyl, (2) C2–10 alkenyl, (3) C2–10 alkynyl, (4) C1–10 alkoxy, (5) C1–10 alkylthio, (6) halogen atom, (7) trihalomethyl, (8) trihalomethoxy, (9) trihalomethylthio, (10) cyano, (11) nitrile, or (12) —$NR^6R^7$, $R^6$ and $R^7$ each independently represents C1–10 alkyl, m and n each independently represents 0 or integer of 1–3, or a nontoxic salt thereof.

2. The tetrahydroquinoline compound according to claim 1, wherein A represents $COOR^1$, or a nontoxic salt thereof.

3. The tetrahydroquinoline compound according to claim 1, wherein A represents 1H-tetrazol-5-yl group, or a nontoxic salt thereof.

4. The tetrahydroquinoline compound according to claim 2, wherein

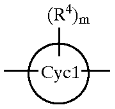 represents 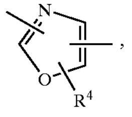, or a nontoxic salt thereof.

5. The tetrahydroquinoline compound according to claim 2, wherein

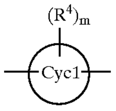 represents 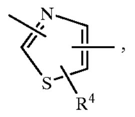, or a nontoxic salt thereof.

6. The tetrahydroquinoline compound according to claim 4, which is (1) 3-(5-(2-(2-(4-methylphenyl)-5-methyloxazol-4-yl)ethoxy)-1,2,3,4-tetrahydroquinolin-1-yl)propanoic acid ethyl ester, (2) 3-(5-(2-(2-(4-trifluoromethylphenyl)-5-methyloxazol-4-yl)ethoxy)-1,2,3,4-tetrahydroquinolin-1-yl)propanoic acid ethyl ester, (3) 3-(5-(2-(2-(4-ethylphenyl)-5-methyloxazol-4-yl)ethoxy)-1,2,3,4-tetrahydroquinolin-1-yl)propanoic acid ethyl ester, (4) 3-(5-(2-(2-(1,3-dioxaindan-5-yl)-5-methyloxazol-4-yl)ethoxy)-1,2,3,4-tetrahydroquinolin-1-yl)propanoic acid ethyl ester, (5) 3-(5-(2-(2-(4-chlorophenyl)-5-methyloxazol-4-yl)ethoxy)-1,2,3,4-tetrahydroquinolin-1-yl)propanoic acid ethyl ester, (6) 3-(5-(2-(2-phenyl-5-methyloxazol-4-yl)ethoxy)-1,2,3,4-tetrahydroquinolin-1-yl)propanoic acid ethyl ester, (7) 3-(5-(2-(2-(4-trifluoromethoxyphenyl)-5-methyloxazol-4-yl)ethoxy)-1,2,3,4-tetrahydroquinolin-1-yl)propanoic acid ethyl ester, (8) 3-(5-(2-(2-(4-methoxyphenyl)-5-methyloxazol-4-yl)ethoxy)-1,2,3,4-tetrahydroquinolin-1-yl)propanoic acid ethyl ester, (9) 3-(5-(2-(2-(4-t-butylphenyl)-5-methyloxazol-4-yl)ethoxy)-1,2,3,4-tetrahydroquinolin-1-yl)propanoic acid ethyl ester,

(10) 3-(5-(2-(2-(4-fluorophenyl)-5-methyloxazol-4-yl)ethoxy)-1,2,3,4-tetrahydroquinolin-1-yl)propanoic acid ethyl ester,

(11) 3-(5-(2-(2-(4-propylphenyl)-5-methyloxazol-4-yl)ethoxy)-1,2,3,4-tetrahydroquinolin-1-yl)propanoic acid ethyl ester,

(12) 3-(5-(2-(2-(4-methylphenyl)-5-methyloxazol-4-yl)ethoxy)-1,2,3,4-tetrahydroquinolin-1-yl)propanoic acid,

(13) 3-(5-(2-(2-(4-trifluoromethylphenyl)-5-methyloxazol-4-yl)ethoxy)-1,2,3,4-tetrahydroquinolin-1-yl)propanoic acid,

(14) 3-(5-(2-(2-(4-ethylphenyl)-5-methyloxazol-4-yl)ethoxy)-1,2,3,4-tetrahydroquinolin-1-yl)propanoic acid,

(15) 3-(5-(2-(2-(1,3-dioxaindan-5-yl)-5-methyloxazol-4-yl)ethoxy)-1,2,3,4-tetrahydroquinolin-1-yl)propanoic acid,

(16) 3-(5-(2-(2-(4-chlorophenyl)-5-methyloxazol-4-yl)ethoxy)-1,2,3,4-tetrahydroquinolin-1-yl)propanoic acid,

(17) 3-(5-(2-(2-phenyl-5-methyloxazol-4-yl)ethoxy)-1,2,3,4-tetrahydroquinolin-1-yl)propanoic acid, 18) 3-(5-(2-(2-(4-trifluoromethoxyphenyl)-5-methyloxazol-4-yl)ethoxy)-1,2,3,4-tetrahydroquinolin-1-yl)propanoic acid,

(19) 3-(5-(2-(2-(4-methoxyphenyl)-5-methyloxazol-4-yl)ethoxy)-1,2,3,4-tetrahydroquinolin-1-yl)propanoic acid,

(20) 3-(5-(2-(2-(4-t-butylphenyl)-5-methyloxazol-4-yl)ethoxy)-1,2,3,4-tetrahydroquinolin-1-yl)propanoic acid,

(21) 3-(5-(2-(2-(4-fluorophenyl)-5-methyloxazol-4-yl)ethoxy)-1,2,3,4-tetrahydroquinolin-1-yl)propanoic acid,

(22) 3-(5-(2-(2-(4-propylphenyl)-5-methyloxazol-4-yl)ethoxy)-1,2,3,4-tetrahydroquinolin-1-yl)propanoic acid,

(23) 3-(5-(2-(2-(4-methylthiophenyl)-5-methyloxazol-4-yl)ethoxy)-1,2,3,4-tetrahydroquinolin-1-yl)propanoic acid,

(24) 3-(7-(2-(2-(4-methylphenyl)-5-methyloxazol-4-yl)ethoxy)-1,2,3,4-tetrahydroquinolin-1-yl)propanoic acid,

(25) 3-(6-(2-(2-(4-methylphenyl)-5-methyloxazol-4-yl)ethoxy)-1,2,3,4-tetrahydroquinolin-1-yl)propanoic acid,

(26) 3-(5-(2-(2-(6-dimethylaminopyridin-3-yl)-5-methyloxazol-4-yl)ethoxy)-1,2,3,4-tetrahydroquinolin-1-yl)propanoic acid,

(27) 3-(5-(2-(2-(4-cyanophenyl)-5-methyloxazol-4-yl)ethoxy)-1,2,3,4-tetrahydroquinolin-1-yl)propanoic acid methyl ester,

(28) 4-(5-(2-(2-(4-methylphenyl)-5-methyloxazol-4-yl)ethoxy)-1,2,3,4-tetrahydroquinolin-1-yl)butanoic acid ethyl ester,

(29) 5-(5-(2-(2-(4-methylphenyl)-5-methyloxazol-4-yl)ethoxy)-1,2,3,4-tetrahydroquinolin-1-yl)pentanoic acid ethyl ester,

(30) 2-(5-(2-(2-(4-methylphenyl)-5-methyloxazol-4-yl)ethoxy)-1,2,3,4-tetrahydroquinolin-1-yl)acetic acid ethyl ester,

(31) 3-(5-(2-(2-(4-cyanophenyl)-5-methyloxazol-4-yl)ethoxy)-1,2,3,4-tetrahydroquinolin-1-yl)propanoic acid,

(32) 4-(5-(2-(2-(4-methylphenyl)-5-methyloxazol-4-yl)ethoxy)-1,2,3,4-tetrahydroquinolin-1-yl)butanoic acid,

(33) 5-(5-(2-(2-(4-methylphenyl)-5-methyloxazol-4-yl)ethoxy)-1,2,3,4-tetrahydroquinolin-1-yl)pentanoic acid, or

(34) 2-(5-(2-(2-(4-methylphenyl)-5-methyloxazol-4-yl)ethoxy)-1,2,3,4-tetrahydroquinolin-1-yl)acetic acid, or a nontoxic salt thereof.

7. The tetrahydroquinoline compound according to claim 5, which is (1) 3-(5-(2-(2-(piperidin-1-yl)-5-methylthiazol-4-yl)ethoxy)-1,2,3,4-tetrahydroquinolin-1-yl)propanoic acid ethyl ester, (2) 3-(5-(2-(2-(piperidin-1-yl)-5-methylthiazol-4-yl)ethoxy)-1,2,3,4-tetrahydroquinolin-1-yl)propanoic acid, or (3) 3-(5-(2-(2-(1,2,5,6-tetrahydropyridin-1-yl)-5-methylthiazol-4-yl)ethoxy)-1,2,3,4-tetrahydroquinolin-1-yl)propanoic acid, or a nontoxic salt thereof.

8. The tetrahydroquinoline compound according to claim 3, which is (1) 5-(2-(2-(4-chlorophenyl)-5-methyloxazol-4-yl)ethoxy)-1-(2-(1H-tetrazol-5-yl)ethyl)-1,2,3,4-tetrahydroquinoline, (2) 5-(2-(2-(4-trifluoromethylphenyl)-5-methyloxazol-4-yl)ethoxy)-1-(2-(1H-tetrazol-5-yl)ethyl)-1,2,3,4-tetrahydroquinoline, (3) 5-(2-(2-(4-fluorophenyl)-5-methyloxazol-4-yl)ethoxy)-1-(2-(1H-tetrazol-5-yl)ethyl)-1,2,3,4-tetrahydroquinoline, or (4) 5-(2-(2-(4-methylphenyl)-5-methyloxazol-4-yl)ethoxy)-1-(2-(1H-tetrazol-5-yl)ethyl)-1,2,3,4-tetrahydroquinoline, or a nontoxic salt thereof.

9. A pharmaceutical composition comprising a tetrahydroquinoline compound of formula (I) described in claim 1, a nontoxic salt thereof as active ingredient.

10. A method for elevating HDL cholesterol in a mammal in need thereof, which comprises administering to said mammal an effective amount of a tetrahydroquinoline derivative compound of the formula (I) depicted in claim 1, or a nontoxic salt thereof.

11. A method for lowering HDL cholesterol or VLDL cholesterol in a mammal in need thereof, which comprises administering to said mammal an effective amount of a tetrahydroquinoline derivative compound of the formula (I) depicted in claim 1, or a nontoxic salt thereof.

* * * * *